US007291713B2

(12) United States Patent
Yamasaki et al.

(10) Patent No.: US 7,291,713 B2
(45) Date of Patent: Nov. 6, 2007

(54) BRANCHED POLYALKYLENE GLYCOLS

(75) Inventors: Motoo Yamasaki, Machida (JP);
Toshiyuki Suzawa, Yamato (JP);
Tatsuya Murakami, Tokyo (JP);
Noriko Sakurai, Tokyo (JP); Kinya Yamashita, Mishima (JP); Mayumi Mukai, Shizuoka (JP); Takashi Kuwabara, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 458 days.

(21) Appl. No.: 10/470,680

(22) PCT Filed: Jan. 30, 2002

(86) PCT No.: PCT/JP02/00709

§ 371 (c)(1),
(2), (4) Date: Jan. 12, 2004

(87) PCT Pub. No.: WO02/060978

PCT Pub. Date: Aug. 8, 2002

(65) Prior Publication Data

US 2005/0063936 A1    Mar. 24, 2005

(30) Foreign Application Priority Data

Jan. 30, 2001    (JP) ............................. 2001-021616

(51) Int. Cl.
*C07K 17/06* (2006.01)
*A61K 31/765* (2006.01)
*A61K 47/48* (2006.01)
*C07D 207/408* (2006.01)

(52) U.S. Cl. .................. 530/351; 424/78.27; 525/54.1; 548/546

(58) Field of Classification Search ................ 548/546; 424/78.27; 530/351; 525/54.1
See application file for complete search history.

(56) References Cited

U.S. PATENT DOCUMENTS

| 3,553,254 | A | * | 1/1971 | Tesoro et al. ............... 560/160 |
| 5,342,940 | A | | 8/1994 | Ono et al. ................. 544/218 |
| 5,643,575 | A | | 7/1997 | Martinez et al. ......... 424/194.1 |
| 5,698,529 | A | | 12/1997 | Alakhov et al. ............... 514/34 |
| 5,767,284 | A | | 6/1998 | Sanchika et al. ........... 548/520 |
| 5,807,971 | A | | 9/1998 | Gozzini et al. ............. 528/332 |
| 5,872,191 | A | | 2/1999 | Sanchika et al. ........... 525/403 |
| 5,919,455 | A | | 7/1999 | Greenwald et al. ....... 424/178.1 |
| 5,932,462 | A | | 8/1999 | Harris et al. ................ 435/188 |
| 6,111,048 | A | | 8/2000 | Asahina et al. ............... 528/45 |
| 2002/0120096 | A1 | | 8/2002 | Tsuchida et al. ............ 528/332 |
| 2003/0219404 | A1 | | 11/2003 | Yamasaki et al. .......... 424/85.4 |

FOREIGN PATENT DOCUMENTS

| EP | 0 400 486 | 12/1990 |
| EP | 0809996 A2 * | 12/1997 |
| EP | 0 839 849 | 5/1998 |
| EP | 0 809 996 | 4/1999 |
| JP | 1153088 | 6/1989 |
| JP | 2000-191700 | 7/2000 |
| WO | WO95/11924 | 5/1995 |
| WO | WO97/10281 | 3/1997 |
| WO | WO99/22770 | 5/1999 |
| WO | WO99/45964 | 9/1999 |
| WO | WO 99/55377 | 11/1999 |
| WO | WO 01/48052 | 7/2001 |

OTHER PUBLICATIONS

Conforti, et al., "PEG Superoxide Dismutase Derivatives: Anti-Inflammatory Activity in Carrageenan Pelurisy in Rats", Pharmacological Research Communications, vol. 19, No. 4 (1987), pp. 287-294.

Yamasaki, et al., "Modification of Recombinant Human Granulocyte Colony-Stimulating Factor (rhG-CSF) and Its Derivative ND 28 with Polyethylene Glycol", J. Biochem, vol. 115, No. 5, (1994), pp. 814-819.

Ahern, et al., ed., Stability of Protein Pharmaceuticals, Part B, Pharmaceutical Biotechnology, vol. 3, "PEG-Modified Proteins" (1992), pp. 235-263.

Ohno, "Polymer-Modification and Polymer Solvent for the Protein Stabilization", Dept. Of Biotechnology, Tokyo University of Agriculture and Technology, vol. 38, No. 5 (1998), pp. 208-210.

Inada, et al., "Ester Synthesis Catalyzed by Polyethylene Glycol-Modified Lipase in Benzene", Biochemical and Biophysical Research Communications, vol. 122, No. 2 (1984) pp. 845-850.

Campbell, et al., Pegylated Peptides V, Journal of Peptide Research, vol. 49 (1997) pp. 527-537.

Goodson, et al., "Site-directed Pegylation of Recombinant Interleukin-2 at its Glycosylation Site", Bio/Technology, vol. 8 (1990) pp. 343-346.

Knauf, et al., "Relationship of Effective Molecular Size to Systemic Clearance in Rats of Recombinant Interleukin-2 Chemically Modified with Water-soluble Polymers", the Journal of Biological Chemistry, vol. 263, No. 29 (1988) pp. 15064-15070.

Pettit, et al., "Structure-Function Studies of Interleukin 15 Using Site-Specific Mutagenesis, Polyethylene Glycol Conjugation, and Homology Modeling", The Journal of Biological Chemistry, vol. 272, No. 4 (1997), pp. 2312-2318.

(Continued)

*Primary Examiner*—Joseph K. McKane
*Assistant Examiner*—Joseph R. Kosack
(74) *Attorney, Agent, or Firm*—Fitzpatrick, Cella, Harper & Scinto

(57) ABSTRACT

The present invention provides a branched polyalkylene glycol wherein three or more single-chain polyalkylene glycols and a group having reactivity with an amino acid side chain, the N-terminal amino group or the C-terminal carboxyl group in a polypeptide or a group convertible into the group having reactivity are bound; and a physiologically active polypeptide modified with the branched polyalkylene glycol.

9 Claims, 2 Drawing Sheets

OTHER PUBLICATIONS

Zeuzem, et al., "Peginterferon alfa-2a (40 kDa) monotherapy: a novel agent for chronic hepatitis C therapy", *Expert Opin. Investig. Drugs* (2001), vol. 12, pp. 2201-2213.

Motzer, et al., "Phase I Trial of 40-kd Branched Pegylated Interferon alfa-2a for Patients With Advanced Renal Cell Carcinoma", *Journal of Clinical Oncology*, vol. 19, No. 5 (Mar. 1, 2001), pp. 1312-1319.

* cited by examiner

BRANCHED POLYALKYLENE GLYCOLS

This application is a filing under 35 U.S.C. 371 of PCT/JP02/00709, which was filed Jan. 30, 2002.

TECHNICAL FIELD

The present invention relates to polyalkylene glycols having a branched structure which are useful as modifiers for polypeptides having a physiological activity (physiologically active polypeptides) and to physiologically active polypeptides modified with the polyalkylene glycols. The present invention also relates to pharmaceutical compositions comprising the physiologically active polypeptides modified with the polyalkylene glycols.

BACKGROUND ART

Physiologically active polypeptides are useful as therapeutic agents for specific diseases. However, they are unstable when administered into blood, and a sufficient pharmacological effect can rarely be expected. For instance, physiologically active polypeptides having a molecular weight of less than 60,000 administered into blood are mostly excreted into urine by renal glomerular filtration, and their use as therapeutic agents is not expected to give a significant therapeutic effect and often requires repeated administration. Some other physiologically active polypeptides are degraded by hydrolases and the like existing in blood, thereby losing their physiological activities. Further, some exogenous physiologically active polypeptides have physiological activities effective for the treatment of diseases, but it is known that such exogenous physiologically active polypeptides and physiologically active polypeptides produced by recombinant DNA techniques sometimes induce immunoreaction when administered into blood to cause serious side-effects such as anaphylactic shock owing to the difference in structure between them and endogenous physiologically active polypeptides. In addition, some physiologically active polypeptides have physical properties unsuitable for use as therapeutic agents, e.g. poor solubility.

One of the known attempts to solve these problems in using physiologically active polypeptides as therapeutic agents is to chemically bind at least one molecule of an inactive polymer chain to physiologically active polypeptides. In many cases, desirable properties are conferred on the polypeptides or proteins by chemically binding polyalkylene glycols such as polyethylene glycol to them.

For example, superoxide dismutase (SOD) modified with polyethylene glycol has a remarkably prolonged half-life in blood and shows a durable action [Pharm. Res. Commun., Vol. 19, p. 287 (1987)]. There is also a report of modification of granulocyte colony-stimulating factor (G-CSF) with polyethylene glycol [J. Biochem., Vol. 115, p. 814 (1994)]. Gillian E. Francis, et al. summarized examples of polyethylene glycol-modified polypeptides such as asparaginase, glutaminase, adenosine deaminase and uricase [Pharm. Biotechnol., Vol. 3, Stability of Protein Pharmaceuticals, Part B, p. 235 (1992), Plenum Press, New York]. Further, it is known that modification of physiologically active polypeptides with polyalkylene glycols give effects such as enhancement of thermal stability [Seibutsubutsuri (Biophysics), Vol. 38, p. 208 (1998)] and solubilization in organic solvents [Biochem. Biophys. Res. Commun.: BBRC, Vol. 122, p. 845 (1984)].

With regard to the methods for binding polyalkylene glycols to peptides or proteins, it is known to introduce an active ester of carboxylic acid, a maleimido group, a carbonate, cyanuric chloride, a formyl group, an oxiranyl group or the like to an end of a polyalkylene glycol and bind it to an amino group or a thiol group in a polypeptide [Bioconjugate Chem., Vol. 6, p. 150 (1995)]. These techniques include the binding of a polyethylene glycol to a specific amino acid residue in a physiologically active polypeptide, which causes enhancement of stability in blood without impairing the biological activities of the peptide or protein. Examples of the polyethylene glycol modification specific to amino acid residues in physiologically active polypeptides include the binding of a polyethylene glycol to the carboxyl terminus of a growth hormone-releasing factor through norleucine as a spacer [J. Peptide Res., Vol. 49, p. 527 (1997)] and the specific binding of a polyethylene glycol to cysteine introduced to the 3-position of interleukin-2 by recombinant DNA techniques [BIO/TECHNOLOGY, Vol. 8, p. 343 (1990)].

Many of the above polyalkylene glycol-modified polypeptides are obtained by binding of linear polyalkylene glycols. However, it has been found that binding of branched polyalkylene glycols is preferable for obtaining chemically modified polypeptides having a high activity. It is generally known that the durability of a chemically modified polypeptide in blood is increased as the molecular weight of a polyalkylene glycol is higher or the modification ratio higher [J. Biol. Chem., Vol. 263, p. 15064 (1988)], but in some cases, the physiological activity of a physiologically active polypeptide is impaired by raising the modification ratio. This is partly because a specific amino group or thiol group in the physiologically active polypeptide which is necessary for its physiological activity is modified with a chemical modifier. For example, it is known that the physiological activity of interleukin-15 lowers according to the modification ratio [J. Biol. Chem., Vol. 272, p. 2312 (1997)].

On the other hand, it is difficult to synthesize high molecular weight polyalkylene glycols having a uniform molecular weight distribution and a high purity. In the case of monomethoxypolyethylene glycols, for example, contamination with diol components as impurities is known. Accordingly, attempts have been made to prepare high molecular weight modifiers by branching currently available polyalkylene glycols having a narrow molecular weight distribution and a high purity. Such attempts provide chemically modified polypeptides having a high physiological activity with a high durability retained even with a decreased modification ratio. Further, it is considered that a larger part of the surface of molecules of physiologically active polypeptides can be covered with polyalkylene glycols by branching of the polyalkylene glycols. For example, double-chain polyethylene glycol derivatives prepared by using cyanuric chloride as the group having a branched structure are known (Japanese Published Unexamined Patent Applications Nos. 72469/91 and 95200/91). In this case, a methoxypolyethylene glycol having an average molecular weight of 5,000 is utilized, but this compound has the problem of toxicity due to the triazine ring. Japanese Published Unexamined Patent Application No. 153088/89 discloses that a chemically modified polypeptide having a high activity can be obtained from a comb-shaped polyethylene glycol which is a copolymer of polyethylene glycol and maleic anhydride at a lower modification ratio compared with a linear polyethylene glycol. However, this compound has many reactive sites for a polypeptide, which causes impairment of the physiological activity of a physiologically active polypeptide, and has an ununiform molecular weight distribution. Also known are a compound having two polyethylene glycol chains through a benzene ring prepared by using cinnamic acid as a material (Japanese Published Unexamined Patent Application No. 88822/91) and compounds having two polyethylene glycol chains prepared by using lysine as a material (WO96/21469, U.S. Pat. No. 5,643,575).

As illustrated by the above examples, compounds having two polyalkylene glycol chains are known, but those having three or more polyalkylene glycol chains have not been produced. Although U.S. Pat. No. 5,643,575 suggests a three-branched, water-soluble, non-antigenic polymer, it contains no disclosure of the method for producing the three-branched compound or of specific examples and provides no information about the excellent effect of the three-branched compound.

There exists a need for a chemically modified polypeptide with improved durability which retains the activity of the physiologically active polypeptide and whose renal glomerular filtration is suppressed. In order to produce the chemically modified polypeptide exhibiting such properties, there is also a need for a modifier with a low toxicity and an improved stability which has an excellent molecular size-increasing effect and a narrow and uniform molecular weight distribution.

DISCLOSURE OF THE INVENTION

An object of the present invention is to provide, as a chemical modifier for a physiologically active polypeptide, a branched chemical modifier having polyalkylene glycol chains which has an excellent molecular size-increasing effect. Another object of the present invention is to provide a physiologically active polypeptide modified with the branched polyalkylene glycol.

The present inventors made intensive studies on branched polyalkylene glycol modifying reagents having a novel structure for modification of physiologically active polypeptides. As a result, the inventors have found that modifying reagents having a molecular size-increasing effect superior to that of known linear or double-chain polyalkylene glycols can be obtained by preparing modifiers having three or more polyalkylene glycol chains. They have further found that modification of physiologically active polypeptides with the above branched polyalkylene glycols gives physiologically active polypeptides modified with branched polyalkylene glycols having three or more chains whose renal glomerular filtration is suppressed to a degree beyond expectation and whose durability in blood is remarkably improved compared with those modified with known linear or double-chain polyalkylene glycols, while retaining their physiological activities.

It has thus been found that the above branched polyalkylene glycols are excellent chemical modifiers and the present invention has been completed.

That is, the present invention provides a branched polyalkylene glycol wherein three or more single-chain polyalkylene glycols and a group having reactivity with an amino acid side chain, the N-terminal amino group or the C-terminal carboxyl group in a polypeptide or a group convertible into the group having reactivity are bound sumultaneously; a physiologically active polypeptide or its derivative modified with the polyalkylene glycol; and a pharmaceutical composition or a therapeutic agent comprising the physiologically active polypeptide or its derivative modified with the polyalkylene glycol. From another viewpoint, the present invention relates to a chemically modified polypeptide wherein a physiologically active polypeptide or its derivative is modified with at least one polyalkylene glycol mentioned above directly or through a spacer; and a pharmaceutical composition or a therapeutic agent comprising the chemically modified polypeptide.

The present invention is described in detail below.

The branched polyalkylene glycols of the present invention include any branched polyalkylene glycols wherein three or more single-chain polyalkylene glycols and a group having reactivity with an amino acid side chain, the N-terminal amino group or the C-terminal carboxyl group in a polypeptide or a group convertible into the group having reactivity are bound. Preferred branched polyalkylene glycols are those wherein three or more single-chain polyalkylene glycols and one to three groups having reactivity with an amino acid side chain, the N-terminal amino group or the C-terminal carboxyl group in a polypeptide or one to three groups convertible into the groups having reactivity are bound. More preferred are branched polyalkylene glycols wherein three or four single-chain polyalkylene glycols and one group having reactivity with an amino acid side chain, the N-terminal amino group or the C-terminal carboxyl group in a polypeptide or one group convertible into the group having reactivity are bound.

The single-chain polyalkylene glycol may be any single-chain polyalkylene glycol but is preferably $R^1\text{-}M_n\text{-}X^1$ (in which M, n, $R^1$ and $X^1$ have the same meanings as defined below).

The group having reactivity with an amino acid side chain, the N-terminal amino group or the C-terminal carboxyl group in a polypeptide or a group convertible into the group having reactivity may be any group having reactivity with an amino acid side chain, the N-terminal amino group or the C-terminal carboxyl group in a polypeptide or any group convertible into the group having reactivity.

Preferred branched polyalkylene glycols of the present invention include compounds represented by formula (I):

$$(R^1\text{-}M_n\text{-}X^1)_m L(X^2\text{—}X^3\text{—}R^2)_q \qquad (I)$$

{wherein L represents a group capable of having four or more branches;

M represents $OCH_2CH_2$, $OCH_2CH_2CH_2$, $OCH(CH_3)CH_2$, $(OCH_2CH_2)_r$—$(OCH_2CH_2CH_2)_s$ (in which r and s, which may be the same or different, each represent an arbitrary positive integer) or $(OCH_2CH_2)_{ra}$—$[OCH(CH_3)CH_2]_{sa}$ (in which ra and sa have the same meanings as the above r and s, respectively);

n represents an arbitrary positive integer;

m represents an integer of 3 or more;

q represents an integer of 1 to 3;

$R^1$ represents a hydrogen atom, lower alkyl or lower alkanoyl;

$R^2$ represents a group having reactivity with an amino acid side chain, the N-terminal amino group or the C-terminal carboxyl group in a polypeptide or a group convertible into the group having reactivity;

$X^1$ represents a bond, O, S, alkylene, $O(CH_2)_{ta}$ (in which ta represents an integer of 1 to 8), $(CH_2)_{tb}O$ (in which tb has the same meaning as the above ta), $NR^3$ (in which $R^3$ represents a hydrogen atom or lower alkyl), $R^4$—NH—C(=O)—$R^5$ [in which $R^4$ represents a bond, alkylene or $O(CH_2)_{tc}$ (in which tc has the same meaning as the above ta) and $R^5$ represents a bond, alkylene or $OR^{5a}$ (in which $R^{5a}$ represents a bond or alkylene)], $R^6$—C(=O)—NH—$R^7$ [in which $R^6$ represents a bond, alkylene or $R^{6a}O$ (in which $R^{6a}$ has the same meaning as the above $R^{5a}$) and $R^7$ represents a bond, alkylene or $(CH_2)_{td}O$ (in which td has the same meaning as the above ta)], $R^8$—C(=O)—O (in which $R^8$ has the same meaning as the above $R^{5a}$) or $O-C(=O)-R^9$ (in which $R^9$ has the same meaning as the above $R^{5a}$);

$X^2$ represents a bond, O or $(CH_2)_{te}O$ (in which te has the same meaning as the above ta);

$X^3$ represents a bond or alkylene; and three or more $R^1$-$M_n$-$X^{1}$'s may be the same or different, and when two or three $X^2$—$X^3$—$R^2$'s are present (when q is 2 or 3), they may be the same or different}

[hereinafter the compounds represented by formula (I) are referred to as Compounds (I), and the same shall apply to the compounds of other formula numbers].

In the definitions of the groups in formula (I), the lower alkyl and the lower alkyl moiety of the lower alkanoyl include linear or branched alkyl groups having 1 to 8 carbon atoms such as methyl, ethyl, n-propyl, isopropyl, n-butyl, isobutyl, sec-butyl, tert-butyl, pentyl, neopentyl, hexyl, heptyl and octyl. The alkylene includes alkylene groups having 1 to 8 carbon atoms such as methylene, ethylene, n-propylene, isopropylene, n-butylene, isobutylene, sec-butylene, tert-butylene, pentylene, neopentylene, hexylene, heptylene and octylene.

In formula (I), M represents $OCH_2CH_2$, $OCH_2CH_2CH_2$, $OCH(CH_3)CH_2$, $(OCH_2CH_2)_r$—$(OCH_2CH_2)_s$ (in which r and s, which may be the same or different, each represent an arbitrary positive integer) or $(OCH_2CH_2)_{ra}$—$[OCH(CH_3)CH_2]_{sa}$ (in which ra and sa have the same meanings as the above r and s, respectively), and when M is $(OCH_2CH_2)_{ra}$—$(OCH_2CH_2CH_2)_s$ (in which r and s have the same meanings as defined above) or $(OCH_2CH_2)_{ra}$—$[OCH(CH_3)CH_2]_{sa}$ (in which ra and sa have the same meanings as defined above), r and s, and ra and sa are preferably 1 to 100,000, more preferably 1 to 1,000.

In formula (I), n represents an arbitrary positive integer and is preferably 10 to 100,000, more preferably 100 to 1,000.

The average molecular weight of the polyalkylene glycol moiety represented by $M_n$ is preferably ca. 1,000 to 1,000,000, more preferably 5,000 to 100,000. When $M_n$ is —$(OCH_2CH_2)_n$—, it is preferred that polyethylene glycols used as starting materials are monodisperse and their molecular weight distribution represented by Mw (weight-average molecular weight)/Mn (number-average molecular weight) is 1.1 or less, and commercially available ones can be utilized when those having an average molecular weight of 30,000 or less are required. For example, monomethoxy-polyethylene glycols having an average molecular weight of 2,000, 5,000, 10,000, 12,000, 20,000 or the like can be used.

In formula (I), q represents an integer of 1 to 3 and is preferably 1.

In formula (I), m represents an integer of 3 or more and is preferably 3 to 4.

The molecular weight of the branched polyalkylene glycols represented by formula (I) is preferably in the range of 500 to 1,000,000.

In formula (I), L represents a group capable of having four or more branches and may have a hydroxyl group, substituted or unsubstituted lower alkyl, lower alkoxy, amino, carboxy, cyano, formyl or the like as a substituent thereon. The lower alkyl and the lower alkyl moiety of the lower alkoxy have the same meaning as the above lower alkyl, and the substituent in the substituted lower alkyl includes a hydroxyl group, amino, lower alkanoyloxy, lower alkanoylamino, lower alkoxy, lower alkoxyalkoxy, lower alkanoyl, lower alkoxycarbonyl, lower alkylcarbamoyl, lower alkylcarbamoyloxy and the like. The lower alkyl moiety of the lower alkanoyloxy, the lower alkanoylamino, the lower alkoxy, the lower alkoxyalkoxy, the lower alkanoyl, the lower alkoxycarbonyl, the lower alkylcarbamoyl and the lower alkylcarbamoyloxy has the same meaning as the above lower alkyl.

As the group capable of having four or more branches represented by L, any group can be used so far as it is capable of binding to a group convertible into a group having reactivity with an amino acid side chain, the N-terminal amino group or the C-terminal carboxyl group in a polypeptide or the group having reactivity through $X^2$—$X^3$, and is capable of having as branches three or more molecules of single-chain polyalkylene glycols through $X^1$. Examples of L include groups formed by removing four or more hydrogen atoms from a polyol or a polycarboxylic acid having a molecular weight of 1,000 or less. Examples of the polyol include low molecular compounds such as glucose, D,L-sorbitol, ribose, erythritol, pentaerythritol, tricine (N-[tris(hydroxymethyl)methyl]glycine), inositol, cholic acid, 3,4,5-trihydroxybenzoic acid (gallic acid), 2,4,6-trihydroxybenzoic acid, 3,4,5-trihydroxybenzaldehyde, quinic acid, shikimic acid and tris(hydroxymethyl)aminomethane, and stereoisomers thereof. Examples of the polycarboxylic acid include low molecular compounds such as 1,4,5,8-naphthalenetetracarboxylic acid, pyromellitic acid, diethylenetriaminepentaacetic acid, 1,2,3,4-butanetetracarboxylic acid, citric acid and γ-carboxyglutamic acid, and stereoisomers thereof.

Examples of preferred L include a group formed by removing four or more hydrogen atoms from tricine, a group formed by removing four or more hydrogen atoms from shikimic acid, a group formed by removing four or more hydrogen atoms from quinic acid, a group formed by removing four or more hydrogen atoms from erythritol, a group formed by removing four or more hydrogen atoms from pentaerythritol, and a group formed by removing four or more hydrogen atoms from glucose.

The structure of the L moiety can be constructed by using a commercially available compound as it is, using the compound through conversion into a derivative suitable for the binding of polyalkylene glycols according to a general organic synthetic method, or using the compound after the protection of a functional group [edited by The Chemical Society of Japan, Jikken Kagaku Koza (Experimental Chemistry Course), fourth edition (1992), Organic Synthesis I-V, Maruzen; PROTECTIVE GROUPS IN ORGANIC SYNTHESIS, second edition, JOHN WILEY & SONS, INC. (1991); etc.]

Cyclohexanes other than those mentioned above can be synthesized according to the method of Kihi, et al. [Daiyukikagaku (Great Organic Chemistry), Vol. 6, p. 183 (1958), Asakura Shoten], the method of G. E. McCasland and E. Clide Horswill [Journal of American Chemical Society, Vol. 76, p. 2373 (1954)] or the like.

In Compound (I), the binding of polyalkylene glycols to L through $X^1$ can be easily effected by combining the reactions known in the general organic synthetic methods [edited by The Chemical Society of Japan, Jikken Kagaku Koza (Experimental Chemistry Course), fourth edition, pp. 19-23 (1992), Organic Synthesis I-V, Maruzen].

In formula (I), $R^2$ represents a group having reactivity with an amino acid side chain, the N-terminal amino group or the C-terminal carboxyl group in a polypeptide or a group convertible into the group having reactivity.

Namely, the above group having reactivity includes groups reactive with any one of the side chains of lysine, cysteine, arginine, histidine, serine, threonine, tryptophan, aspartic acid, glutamic acid, glutamine and the like, the N-terminal amino group and the C-terminal carboxyl group in a polypeptide. Examples of such groups include a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryldisulfido, and azido.

In the definitions of the above groups, the lower alkyl moiety of the lower alkoxycarbonyloxy, the halogenated lower alkyl, the lower alkanoyloxy and the lower alkanoyloxycarbonyl has the same meaning as the above lower alkyl. The aryl moiety of the aryloxycarbonyl, the aryloxycarbonyloxy and the aryldisulfido includes aryls having 6 to 14 carbon atoms such as phenyl, naphthyl, biphenyl and anthryl. The aroyl moiety of the aroyloxycarbonyl includes aroyls having 7 to 13 carbon atoms such as benzoyl, naphthoyl and phthaloyl. The halogen moiety of the halogenated carbonyl and the halogenated lower alkyl includes atoms of fluorine, chlorine, bromine and iodine.

The substituted lower alkoxycarbonyloxy has 1 to 3 substituents which may be the same or different. Examples of the substituents are a hydroxyl group, carboxy and halogen. The halogen has the same meaning as defined above.

The substituted aryloxycarbonyl, the substituted aryloxycarbonyloxy, the substituted aryldisulfido and the subsituted aroyloxycarbonyl have 1 to 3 substituents which may be the same or different. Examples of the substituents are a hydroxyl group, carboxy, halogen, cyano and lower alkyl. The halogen and the lower alkyl have the same meanings as defined above, respectively.

The group represented by $R^2$ may be contained in the starting material for constructing the structure of the L moiety, or may be formed by protecting a necessary functional group in the starting material with an appropriate protective group in advance [PROTECTIVE GROUPS IN ORGANIC SYNTHESIS, second edition, JOHN WILEY & SONS, INC. (1991) etc.], removing the protective group after binding polyalkylene glycols to L through $X^1$'s to make branches, and converting it, if necessary. Further, after polyalkylene glycols are bound to L through $X^1$'s to make branches, the above $R^2$ can also be introduced to L, if necessary through $X^2$ or $X^3$, by a usual organic synthetic method.

More specifically, the branched polyalkylene glycols of the present invention can be produced, for example, by the following processes. The processes for producing the branched polyalkylene glycols of the present invention are not limited thereto.

Process 1: Production of compounds wherein $X^1$ is a bond, O, alkylene, $O(CH_2)_{ta}$ or $(CH_2)_{tb}O$ Compound (Ia), i.e. Compound (I) wherein $X^1$ is a bond, O, alkylene, $O(CH_2)_{ta}$ (in which ta has the same meaning as defined above) or $(CH_2)_{tb}O$ (in which tb has the same meaning as defined above) can be produced, for example, by the following process.

A polyol having three or more hydroxyl groups is dissolved or suspended in an appropriate solvent (e.g. N,N-dimethylformamide, dimethyl sulfoxide, toluene, tetrahydrofuran, acetonitrile or pyridine) under anhydrous conditions, and 3 mol or more of a halide or tosylate of a polyalkylene glycol or a monoalkyl ether or monocarboxylate ester thereof (hereinafter, they are collectively referred to as polyalkylene glycol A) is added thereto in the presence of 1 to 30 mol of an appropriate base (e.g. sodium hydride, zinc oxide, sodium hydroxide or triethylamine), followed by reaction at −20 to 150° C. for 1 hour to 10 days to obtain a mixture containing a branched polyalkylene glycol having three or more chains.

The polyol is selected from commercially available compounds such as quinic acid, glucose, sorbitol, ribose, erythritol, pentaerythritol, tricine and inositol, and compounds derived from the commercially available compounds. Examples of the compounds derived from the commercially available compounds include polyols obtained by reducing polycarboxylic acid selected from ethylenediaminetetraacetic acid, 1,2,4,5-benzenetetracarboxylic acid, γ-carboxyglutamic acid and the like with an appropriate reducing agent according to a usual organic synthetic method [edited by The Chemical Society of Japan, Jikken Kagaku Koza (Experimental Chemistry Course), fourth edition, Vols. 19-21 (1992), Maruzen]. Suitable reducing agents include lithium aluminum hydride, sodium borohydride, sodium cyanoborohydride and hydrogen.

The polyol may have hydroxyl groups at any positions and can be used in the reaction after appropriate protection of a functional group unnecessary for the reaction by the method described in PROTECTIVE GROUPS IN ORGANIC SYNTHESIS, second edition, JOHN WILEY & SONS, INC. (1991), etc. or conversion into a derivative.

The halide or tosylate of polyalkylene glycol A can readily be produced by various methods disclosed in a review by Samuel Zalipsky [Bioconjugate Chem., Vol. 6, p. 150 (1995)] and the like. The halide or tosylate of polyalkylene glycol A used for the binding may have any average molecular weight so long as the molecular weight distribution is uniform (preferably Mw/Mn is 1.1 or less).

The obtained mixture containing a branched polyalkylene glycol having three or more chains can be used in the next step at the purity as it is or after purifying and isolating the branched polyalkylene glycol having three, four, five or more chains to a desired purity according to the number of branches by a known method such as ion-exchange chromatography, reversed phase chromatography, hydrophobic chromatography, two-phase partition or recrystallization. By the above steps, some of Compounds (Iaj), i.e. Compounds (Ia) wherein $R^2$ is a hydroxyl group are obtained.

On the other hand, the desired branched polyalkylene glycol having three or more chains can also be prepared by using a polyhalide or a polytosyl and polyalkylene glycol A. In this case, the desired compound can be obtained by dissolving or suspending 3 molar equivalents or more of polyalkylene glycol A in an appropriate solvent (e.g. N,N-dimethylformamide, dimethyl sulfoxide, toluene or tetrahydrofuran), and adding 1 molar equivalent of a polyhalide or polytosyl thereto in the presence of 1 to 30 mol of an appropriate base (e.g. sodium hydride, zinc oxide, sodium hydroxide or triethylamine) per mol of polyalkylene glycol A, followed by reaction at −20 to 150° C. for 1 hour to 10 days.

The polyhalide may be a commercially available compound or may be obtained by converting the above polyol into a halide [edited by The Chemical Society of Japan, Jikken Kagaku Koza (Experimental Chemistry Course), fourth edition, Vol. 19 (1992), Maruzen]. The polytosyl can be obtained by dissolving or suspending the polyol in an appropriate solvent (e.g. N,N-dimethylformamide, dimethyl sulfoxide, toluene, tetrahydrofuran, acetonitrile or pyridine), and adding thereto 1 to 3 molar equivalents (based on the hydroxyl group) of a tosyl halide in the presence of 1 to 30 mol (based on the hydroxyl group) of an appropriate base (e.g. sodium hydride, zinc oxide, sodium hydroxide, triethylamine or potassium naphthalene), followed by reaction at −20 to 150° C. for 1 hour to several days.

Then, $R^2$ is introduced into the obtained mixture containing a branched polyalkylene glycol having three or more chains or a compound purified therefrom. As $R^2$, a functional group remaining in a polyol, a polyhalide or a polytosyl can be utilized as it is after polyalkylene glycol A or a halide or tosylate thereof is bound to the polyol, polyhalide or polytosyl. Alternatively, a functional group bound to a polyol is protected in advance, and after polyalkylene glycol A or a halide or tosylate thereof is bound, a group obtained by removing the protecting group of the functional group may be utilized as $R^2$. In this case, after at least one hydroxyl group or other functional group in the above polyol, polyhalide or polytosyl is protected with an appropriate protective group, polyalkylene glycol A or a halide or tosylate thereof is introduced to the other hydroxyl groups, halogen or tosyl group moiety by the same method as above to synthesize a compound with three or more polyalkylene glycol chains bound, and then the functional group from which the protective group is removed is utilized as such, or at least one of the functional groups is converted to $R^2$ according to the method described below. The functional groups present in the polyol, polyhalide or polytosyl before or after binding polyalkylene glycol A or a halide or tosylate thereof include carboxy, amino, halogen, cyano, formyl, carbonyl and the like, in addition to a hydroxyl group. As for the protective groups for functional groups, suitable protective groups for a hydroxyl group include benzyl, tert-butyl, acetyl, benzyloxycarbonyl, tert-butyloxycarbonyl, dimethyl-tert-butylsilyl, diphenyl-tert-butylsilyl, trimethylsilyl, triphenylsilyl, tosyl and tetrahydropyranyl; those for amino include methyl, ethyl, 9-fluorenylmethyloxycarbonyl, benzyloxycarbonyl, nitrobenzyloxycarbonyl, N-phthalimido, acetyl and tert-butyloxycarbonyl; those for carboxy include benzyl, methyl, ethyl, tert-butyl, 9-fluorenylmethyl, methoxyethoxymethyl, 2,2,2-trichloroethyl, 2-(trimethylsilyl)ethyl, cinnamoyl, allyl and nitrophenyl; and those for formyl include dimethyl acetal, diethyl acetal, dibenzyl acetal and 1,3-dioxanyl [PROTECTIVE GROUPS IN ORGANIC SYNTHESIS, second edition, JOHN WILEY & SONS, INC. (1991)].

Examples of the polyols, polyhalides and polytosyls having a functional group that can be utilized as $R^2$, as such or through introduction and removal of a protective group, and being useful as a starting material for constructing the structure of the L moiety include shikimic acid, quinic acid, 3,4,5-trihydroxybenzoic acid, cholic acid, and halides and tosylates thereof.

Among Compounds (I), those obtained by introducing substituent $R^2$ into compounds having L can readily be produced, for example, by the following processes.

Process 1-1

Among Compounds (Ia), those wherein $R^2$ is carboxy, i.e. compounds represented by formula (Iaa):

$$(R^1\text{-}M_n\text{-}X^{1a})_m L(X^2\text{—}X^3\text{—}COOH)_q \qquad (Iaa)$$

(wherein $X^{1a}$ represents a bond, O, alkylene, $O(CH_2)_{ta}$ or $(CH_2)_{tb}O$; and $R^1$, L, M, n, m, q, $X^2$ and $X^3$ have the same meanings as defined above, respectively); those wherein $R^2$ is carbamoyl, i.e. compounds represented by formula (Iab):

$$(R^1\text{-}M_n\text{-}X^{1a})_m L(X^2\text{—}X^3\text{—}CONH_2)_q \qquad (Iab)$$

(wherein $R^1$, L, M, n, m, q, $X^{1a}$, $X^2$ and $X^3$ have the same meanings as defined above, respectively); and those wherein $R^2$ is cyano, i.e. compounds represented by formula (Iac):

$$(R^1\text{-}M_n\text{-}X^{1a})_m L(X^2\text{—}X^3\text{—}CN)_q \qquad (Iac)$$

(wherein $R^1$, L, M, n, m, q, $X^{1a}$, $X^2$ and $X^3$ have the same meanings as defined above, respectively) can be synthesized, for example, in the following manner.

Compound (Iaa), Compound (Iab) and Compound (Iac) can be obtained by reacting a reaction mixture containing (Iaj), i.e. Compound (Ia) having a hydroxyl group as $R^2$ among Compounds (Ia) obtained by Process 1 using a polyol, or the compound purified from the mixture with 1 to 30 molar equivalents of acrylic acid, acrylamide, acrylonitrile or the like in an appropriate solvent (e.g. water, methylene chloride, toluene or tetrahydrofuran) in the presence of a base (catalytic amount or 1 to 20%) at −20 to 150° C. for 1 hour to several days. Suitable bases include potassium hydroxide, sodium hydroxide and sodium hydride. Compound (Iaa) can also be obtained by dissolving or suspending a reaction mixture containing Compound (Iaj) obtained by Process 1 or the compound purified therefrom in an appropriate solvent (e.g. N,N-dimethylformamide, dimethyl sulfoxide, toluene or tetrahydrofuran) under anhydrous conditions, and reacting the compound with 1 to 50 molar equivalents of α-halogenated acetic acid ester in the presence of 1 to 50 mol of an appropriate base (e.g. sodium hydride, zinc oxide, sodium hydroxide or triethylamine) at −20 to 150° C. for 1 hour to several days, followed by hydrolysis. Further, Compound (Iaa) can be obtained by dissolving or suspending Compound (Iaj) obtained by Process 1 in an appropriate solvent (e.g. N,N-dimethylformamide, dimethyl sulfoxide, toluene or tetrahydrofuran), and reacting the compound with 1 to 50 mol of an activating agent (e.g. succinimidyl carbonate, p-nitrophenyl chloroformate or carbonyldiimidazole) in the presence of 1 to 50 mol of an appropriate base (e.g. sodium hydride, zinc oxide, sodium hydroxide or triethylamine) at −20 to 100° C. for 1 hour to 10 days to activate the compound, followed by reaction with an amino acid such as γ-aminobutyric acid, glycine or β-alanine, or a derivative thereof.

It is also possible to produce Compound (Iaa) by reacting Compound (Iaj) obtained by Process 1 with an acid anhydride such as succinic anhydride or glutaric anhydride in the presence of the same base as above.

Moreover, Compound (Iaa) can be obtained by, after producing Compound (Iai), i.e. Compound (Ia) wherein $R^2$ is halogenated lower alkyl according to Process 1 using a polyhalide, dissolving or suspending hydroxycarboxylate, malonate, γ-aminobutyrate, an ester of β-alanine, an ester of glycine or the like in an appropriate solvent (e.g. N,N-dimethylformamide, dimethyl sulfoxide, toluene or tetrahydrofuran), adding Compound (Iai) thereto in the presence of 1 to 50 mol of an appropriate base (e.g. sodium hydride, zinc oxide, sodium hydroxide or triethylamine), and reacting them at −20 to 150° C. for 1 hour to several days, followed by hydrolysis.

Furthermore, Compound (Iaa) can be obtained by substituting at least one hydroxyl group or halogen of the above polyol or polyhalide with a residue containing carboxylic acid or protected carboxylic acid in advance, and then substituting the remaining three or more hydroxyl groups or halogens of the polyol or polyhalide with polyalkylene glycol A or a halide or tosylate thereof according to the method shown in Process 1. In this case, the introduction of the residue containing carboxylic acid or protected carboxylic acid can be carried out in a manner similar to the above. When carboxylic acid is protected, the protective group is removed after the introduction of polyalkylene glycol A or a halide or tosylate thereof into the polyol or polyhalide to form free carboxylic acid.

The compound converted into carboxylic acid can be purified and isolated at a desired purity according to a known method such as anion-exchange chromatography, hydrophobic chromatography, reversed phase chromatography, two-phase partition or recrystallization.

Process 1-2

Among Compounds (Ia), those wherein $R^2$ is amino, i.e. compounds represented by formula (Iad):

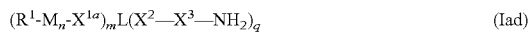

(Iad)

(wherein $R^1$, L, M, n, m, q, $X^{1a}$, $X^2$ and $X^3$ have the same meanings as defined above, respectively) can be obtained, for example, by treating Compound (Iac) obtained by Process 1-1 with an appropriate reducing agent. Suitable reducing agents include lithium aluminum hydride, sodium borohydride, sodium cyanoborohydride and hydrogen.

Compound (Iad) can also be obtained by reacting Compound (Iai) obtained by Process 1 or a compound wherein the halogen moiety of Compound (Iai) is substituted with a tosyl group, with 5 equivalents to an excess amount of a diamine such as ethylenediamine or propylenediamine in the presence of an appropriate base.

Further, similarly to Process 1-1, Compound (Iad) can be obtained by dissolving or suspending Compound (Iaj) in an appropriate solvent (e.g. N,N-dimethylformamide, dimethyl sulfoxide, toluene or tetrahydrofuran), and reacting the compound with 1 to 50 mol of an activating agent (e.g. succinimidyl carbonate, p-nitrophenyl chloroformate or carbonyldiimidazole) in the presence of 1 to 50 mol of an appropriate base (e.g. sodium hydride, zinc oxide, sodium hydroxide or triethylamine) at −20 to 100° C. for 1 hour to 10 days to activate the compound, followed by reaction with 1 equivalent to an excess amount of a diamine such as ethylenediamine or propylenediamine in the presence of an appropriate base.

Furthermore, Compound (Iad) can be obtained, in accordance with the method shown in Process 1, by introducing at least one amino or protected amino into a compound such as a polyol used for forming L in advance, and then substituting the remaining three or more hydroxyl groups or halogen moieties of the compound with polyalkylene glycol A or a halide or tosylate thereof.

Among Compounds (Ia), those wherein $R^2$ is maleimido, i.e. compounds represented by formula (Iae):

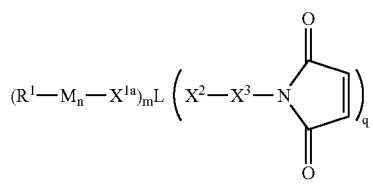

(Iae)

(wherein $R^1$, L, M, n, m, q, $X^{1a}$, $X^2$ and $X^3$ have the same meanings as defined above, respectively) can be obtained, for example, by reacting Compound (Iad) with N-alkoxycarbonylmaleimide in a saturated aqueous solution of sodium hydrogencarbonate according to the method of Oskar Keller, et al. [Helv. Chim. Acta, Vol. 58, p. 531 (1975)] or the method of Timothy P. Kogan, et al. [Synthetic Commun., Vol. 22, p. 2417 (1992)]. As the N-alkoxycarbonylmaleimide, N-ethoxycarbonylmaleimide and N-methoxycarbonylmaleimide can be used.

Compound (Iae) can also be obtained, in accordance with the method shown in Process 1, by introducing at least one maleimido into a compound such as a polyol used for forming L in advance, and then substituting the remaining three or more hydroxyl groups or halogen moieties of the compound with polyalkylene glycol A or a halide or tosylate thereof.

Compound (Iad), Compound (Iae) and synthetic intermediates thereof can be isolated and purified to a desired purity according to the number of branches of polyalkylene glycol by the same methods as above.

Process 1-3

Among Compounds (Ia), those wherein $R^2$ is formyl, i.e. compounds represented by formula (Iaf):

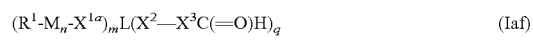

(Iaf)

(wherein $R^1$, L, M, n, m, q, $X^{1a}$, $X^2$ and $X^3$ have the same meanings as defined above, respectively) can be obtained, for example, by oxidizing Compound (Iag), i.e. Compound (Ia) having hydroxylmethyl as $R^2$ obtained by Process 1 with an appropriate oxidizing agent. Suitable oxidizing agents include pyridinium chlorochromate, chromic acid, silver ion and dimethyl sulfoxide. Compound (Iaf) can also be obtained by reducing Compound (Iaa) with an appropriate reducing agent in a manner similar to the above.

Moreover, formyl can be introduced by binding aminoethyl acetal, hydroxyethyl acetal, halogenated ethyl acetal, halogenated methyl acetal or the like to Compound (Iaj) or Compound (Iai) obtained by Process 1 or a compound wherein the halogen moiety of Compound (Iai) is substituted with a tosyl group, and then removing acetal.

Similarly, using Compound (Iaj) obtained by Process 1, formyl can also be introduced by activating a hydroxyl group according to the method shown in Process 1-1, binding aminoethyl acetal, hydroxyethyl acetal or the like, and then removing acetal.

Compound (Iaf) can also be obtained, in accordance with the method shown in Process 1, by introducing at least one aldehyde or protected aldehyde into a compound such as a polyol used for forming L in advance, and then substituting the remaining three or more hydroxyl groups or halogen moieties of the compound with polyalkylene glycol A or a halide or tosylate thereof.

Compound (Iaf) and synthetic intermediates thereof can be isolated and purified to a desired purity according to the number of branches of polyalkylene glycol by the same methods as above.

Process 1-4

Among Compounds (Ia), those wherein $R^2$ is halogenated carbonyl, i.e. compounds represented by formula (Iah):

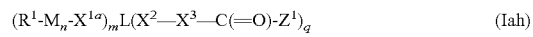

(Iah)

(wherein $Z^1$ represents a halogen; and $R^1$, L, M, n, m, q, $X^{1a}$, $X^2$ and $X^3$ have the same meanings as defined above, respectively) can be obtained, for example, by heating Compound (Iaa) having carboxy as $R^2$ in thionyl halide or in an appropriate mixed solvent of thionyl halide and toluene, dimethylformamide or the like in the presence of an appropriate catalyst (e.g. pyridine or triethylamine) at 0 to 150° C. for 1 to 24 hours.

The halogen in the halogenated carbonyl has the same meaning as the above halogen.

Process 1-5

Among Compounds (Ia), those wherein $R^2$ is halogenated lower alkyl, i.e. compounds represented by formula (Iai):

$$(R^1\text{-}M_n\text{-}X^{1a})_m L(X^2\text{—}X^3\text{-}Z^2)_q \qquad \text{(Iai)}$$

(wherein $Z^2$ represents a halogenated lower alkyl; and $R^1$, L, M, n, m, q, $X^{1a}$, $X^2$ and $X^3$ have the same meanings as defined above, respectively) can be obtained, for example, by heating Compound (Iaj) having a hydroxyl group as $R^2$ in thionyl halide or in an appropriate mixed solvent of thionyl halide and toluene, dimethylformamide or the like in the presence of an appropriate catalyst (e.g. pyridine or triethylamine) at 0 to 150° C. for 1 to 24 hours.

The halogen and the lower alkyl moiety in the halogenated lower alkyl have the same meanings as defined above, respectively.

Compound (Iai) can also be obtained by reacting Compound (Iaj) obtained by Process 1 or Compound (Iad) having amino as $R^2$ with 5 equivalents to an excess amount of dihalogenated alkyl such as dibromoethane or dibromopropane in the presence of an appropriate base as described above.

Further, Compound (Iai) can be obtained, in accordance with the method shown in Process 1 above, by introducing at least one halogenated lower alkyl into a compound such as a polyol used for forming L in advance, and then substituting the remaining three or more hydroxyl groups or halogen moieties of the compound with polyalkylene glycol A or a halide or tosylate thereof.

Compound (Iai) and synthetic intermediates thereof can be isolated and purified to a desired purity according to the number of branches of polyalkylene glycol by the same methods as above.

Process 1-6

Among Compounds (Ia), those wherein $R^2$ is isocyanato, i.e. compounds represented by formula (Iak):

$$(R^1\text{-}M_n\text{-}X^{1a})_m L(X^2\text{—}X^3\text{—}N\text{=}C\text{=}O)_q \qquad \text{(Iak)}$$

(wherein $R^1$, L, M, n, m, q, $X^{1a}$, $X^2$ and $X^3$ have the same meanings as defined above, respectively) can be obtained, for example, by reacting Compound (Iad) with phosgene or oxalyl chloride in an appropriate solvent (e.g. toluene, tetrahydrofuran or methylene chloride) at 0 to 150° C. for 1 to 24 hours, or by reacting the compound with N,N'-carbonyldiimidazole, followed by decomposition at room temperature.

Compound (Iap), i.e. Compound (Ia) wherein $R^2$ is isothiocyanato (—N=C=S) can be produced according to the same process as above except that thiophosgene is used in place of phosgene.

Process 1-7

Among Compounds (Ia), those wherein $R^2$ is succinimidooxycarbonyl, substituted or unsubstituted aryloxycarbonyl, benzotriazolyloxycarbonyl or phthalimidooxycarbonyl, i.e. compounds represented by formula (Ial):

$$(R^1\text{-}M_n\text{-}X^{1a})_m L(X^2\text{—}X^3\text{—}R^{2a})_q \qquad \text{(Ial)}$$

(wherein $R^{2a}$ represents succinimidooxycarbonyl, substituted or unsubstituted aryloxycarbonyl, benzotriazolyloxycarbonyl or phthalimidooxycarbonyl; and $R^1$, L, M, n, m, q, $X^{1a}$, $X^2$ and $X^3$ have the same meanings as defined above, respectively) can be produced by ordinary methods for synthesizing esters.

For example, the desired compound can be obtained by reacting 1 mol of Compound (Iaa) with 1 to 10 mol of N-hydroxysuccinimide, substituted or unsubstituted hydroxyaryl, N-hydroxybenzotriazole or N-hydroxyphthalimide in the presence of 1 to 10 mol of a condensing agent (e.g. N,N'-dicyclohexylcarbodiimide) in an appropriate solvent (e.g. dimethylformamide, methylene chloride or dimethyl sulfoxide) at −20 to 100° C. for 1 to 24 hours. More specifically, the desired compound can be obtained according to the method of introducing a carboxyl group to an end of polyalkylene glycol, the method of producing N-hydroxysuccinimide ester of carboxymethylpolyalkylene glycol, or the like by A. Fradet, et al. [Polym. Bull., Vol. 4, p. 205 (1981)] or K. Geckeler, et al. [Polym. Bull., Vol. 1, p. 691 (1979)].

The substituted or unsubstituted aryloxycarbonyl has the same meaning as defined above. The aryl moiety of the hydroxyaryl has the same meaning as the aryl moiety of the aryloxycarbonyl, and the substituent in the substituted hydroxyaryl has the same meaning as the substituent in the substituted aryloxycarbonyl.

Process 1-8

Among Compounds (Ia), those wherein $R^2$ is vinylsulfonyl, i.e. compounds represented by formula (Iam):

$$(R^1\text{-}M_n\text{-}X^{1a})_m L(X^2\text{—}X^3\text{—}SO_2\text{—}CH\text{=}CH_2)_q \qquad \text{(Iam)}$$

(wherein $R^1$, L, M, n, m, q, $X^{1a}$, $X^2$ and $X^3$ have the same meanings as defined above, respectively) can be produced, for example, by the method of Margherita Morpurgo, et al. [Bioconjugate Chem., Vol. 7, p. 363 (1996)] using Compound (Iaj).

Process 1-9

Among Compounds (Ia), those wherein $R^2$ is substituted or unsubstituted lower alkoxycarbonyloxy or substituted or unsubstituted aryloxycarbonyloxy, i.e. compounds represented by formula (Ian):

$$(R^1\text{-}M_n\text{-}X_{1a})_m L(X^2\text{—}X^3\text{—}R^{2b}) \qquad \text{(Ian)}$$

(wherein $R^{2b}$ represents substituted or unsubstituted lower alkoxycarbonyloxy or substituted or unsubstituted aryloxycarbonyloxy; and $R^1$, L, M, n, m, q, $X^{1a}$, $X^2$ and $X^3$ have the same meanings as defined above, respectively) can be obtained, for example, by reacting Compound (Iaj) having a hydroxyl group as $R^2$ with an excess amount of p-nitrophenyl chloroformate, ethyl chloroformate or the like in the presence of a base (e.g. dimethylaminopyridine or triethylamine) according to the method of Talia Miron and Meir Wilchek [Bioconjugate Chem., Vol. 4, p. 568 (1993)].

Compound (Ian) can also be obtained, in accordance with the method shown in Process 1, by introducing at least one substituted or unsubstituted alkoxycarbonyloxy or substituted or unsubstituted aryloxycarbonyloxy into a compound such as a polyol used for forming L in advance, and then substituting the remaining three or more hydroxyl groups or halogen moieties of the compound with polyalkylene glycol A or a halide or tosylate thereof.

Compound (Ian) and synthetic intermediates thereof can be isolated and purified to a desired purity according to the number of branches of polyalkylene glycol by the same methods as above.

The substituted or unsubstituted lower alkoxycarbonyloxy and the substituted or unsubstituted aryloxycarbonyloxy have the same meanings as defined above, respectively.

Process 2: Compounds wherein $X^1$ is S

Compound (Ib), i.e. Compound (I) wherein $X^1$ is S can be obtained, for example, in a manner similar to that in Process 1, by reacting a compound obtained by converting a polyol into a polyhalide [edited by The Chemical Society of Japan, Jikken Kagaku Koza (Experimental Chemistry Course), fourth edition, Vol. 19 (1992), Maruzen] or a commercially available polyhalide with a thiol derivative of polyalkylene glycol A in an appropriate solvent in the presence of an appropriate base.

Compound (Ib) can also be obtained, in reverse to the above step, by reacting a halide or tosylate of polyalkylene glycol A with a polythiol.

The thiol derivative of polyalkylene glycol A may be a commercially available product or may be prepared by the methods summarized by Samuel Zalipsky, et al. [Bioconjugate Chem., Vol. 6, p. 150 (1995)].

The reaction conditions and purification conditions in each step are similar to those in Process 1.

Process 2-1

Among Compounds (Ib), those wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy, or substituted or unsubstituted aryloxycarbonyloxy can be obtained by producing the compound wherein $X^1$ is —S— according to Process 2, and then combining the methods described in Process 1-1 to Process 1-9.

Process 3: Compounds wherein $X^1$ is $NR^3$

Compound (Ic), i.e. Compound (I) wherein $X^1$ is $NR^3$ (in which $R^3$ has the same meaning as defined above) can be obtained, for example, in a manner similar to that in Process 1, by reacting a compound obtained by converting a polyol into a polyamine or a commercially available polyamine with a halide or tosylate of polyalkylene glycol A in an appropriate solvent in the presence of an appropriate base.

Compound (Ic) can also be obtained by reacting an amino derivative of polyalkylene glycol A with a polyhalide.

Moreover, Compound (Ic) can be obtained by dissolving or suspending a polyaldehyde (1 equivalent) and an amino derivative of polyalkylene glycol A (1 to 30 equivalents per formyl group in the polyaldehyde) in an appropriate solvent (e.g. methanol, ethanol, dimethylformamide, acetonitrile, dimethyl sulfoxide, water or buffer), and reacting them in the presence of a reducing agent (e.g. sodium cyanoborohydride or sodium borohydride; 1 to 30 equivalents per formyl group in the polyaldehyde) at −20 to 100° C.

Further, Compound (Ic) can be produced by using a polyamine and an aldehyde derivative of polyalkylene glycol A.

As the above polyaldehyde, a commercially available one may be used as it is. Also useful are a compound obtained by oxidizing a polyalcohol, and a compound obtained by reducing a polycarboxylic acid. The aldehyde derivative of polyalkylene glycol A may be a commercially available product, or may be prepared by oxidizing alcohol at an end of polyalkylene glycol A.

The reaction conditions and purification conditions in each step are similar to those in Process 1.

Process 3-1

Among Compounds (Ic), those wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy, or substituted or unsubstituted aryloxycarbonyloxy can be obtained by synthesizing Compound (Ic) according to Process 3, and then combining the methods described in Process 1-1 to Process 1-9.

Process 4: Compounds wherein $X^1$ is $R^4$—NH—C(=O)—$R^5$ or $R^6$—C(=O)—NH—$R^7$ Compound (Ida), i.e. Compound (I) wherein $X^1$ is $R^4$—NH—C(=O)—$R^5$ (in which $R^4$ and $R^5$ have the same meanings as defined above, respectively) can be obtained, for example, by dissolving or suspending a polycarboxylic acid compound selected from γ-carboxyglutamic acid, citric acid, 1,2,3,4-butanetetracarboxylic acid, etc. in an appropriate solvent (e.g. N,N-dimethylformamide or dimethyl sulfoxide), adding an alcohol compound (e.g. N-hydroxysuccinimide, N-hydroxyphthalimide, N-hydroxybenzotriazole or p-nitrophenol; 1 to 30 equivalents per carboxyl group in the polycarboxylic acid compound) and a condensing agent (e.g. N,N'-dicyclohexylcarbodiimide or benzotriazol-1-yloxytripyrrolidinophosphonium hexafluorophosphate; 1 to 30 equivalents per carboxyl group in the polycarboxylic acid compound), further adding an amino derivative of polyalkylene glycol A (1 to 30 equivalents per carboxyl group in the polycarboxylic acid compound), and reacting them according to a peptide synthetic method [Izumiya, et al., Peptide Gosei no Kiso to Jikken (Basis and Experiment of Peptide Synthesis) (1985), Maruzen]. The reaction is carried out with stirring under anhydrous conditions at −20 to 100° C. for 1 hour to 10 days.

It is also possible to obtain a reaction mixture containing a branched polyethylene glycol derivative having three or more chains wherein $R^2$ is carboxy at a high purity by protecting at least one carboxyl group in a polycarboxylic acid molecule with an appropriate protective group (e.g. methyl, ethyl, benzyl or tert-butyl), introducing an amino derivative of polyalkylene glycol A to the remaining carboxyl groups by the above method, and then removing the protective group of the carboxyl group by a usual deprotection method. In this case, the introduction and removal of the protective group of carboxylic acid can be carried out by using methods employed in ordinary peptide synthesis [Izumiya, et al., Peptide Gosei no Kiso to Jikken (Basis and Experiment of Peptide Synthesis) (1985), Maruzen]. The configuration of carboxyl groups in the polycarboxylic acid may be any configuration including steric configuration. The amino derivative of polyalkylene glycol A used above may have any average molecular weight so long as the molecular weight distribution is uniform (preferably Mw/Mn is 1.1 or less).

Compound (Idb), i.e. Compound (I) wherein $X^1$ is $R^6$—C(=O)—NH—$R^7$ (in which $R^6$ and $R^7$ have the same meanings as defined above, respectively) can also be obtained, in reverse to the above step, by reacting a polyamine with an active ester of a carboxylic acid derivative of polyalkylene glycol A or an acid halide derivative of polyalkylene glycol A. The acid halide derivative of polyalkylene glycol A can be obtained by heating a carboxylic acid derivative of polyalkylene glycol A in thionyl halide or in an appropriate mixed solvent of thionyl halide and toluene, dimethylformamide or the like in the presence of an appropriate catalyst (e.g. pyridine or triethylamine) at 0 to 150° C. for 1 to 24 hours.

The reaction conditions and purification conditions in each step are similar to those in the above processes.

Process 4-1

Among Compounds (Ida) and (Idb), those wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy, or substituted or unsubstituted aryloxycarbonyloxy can be obtained by synthesizing Compound (Ida) or Compound (Idb) according to Process 4, and then combining the methods described in Process 1-1 to Process 1-9.

Process 5: Compounds wherein $X^1$ is $R^8$—C(=O)—O or O—C(=O)—$R^9$

Compound (Ie), i.e. Compound (I) wherein $X^1$ is $R^8$—C(=O)—O (in which $R^8$ has the same meaning as defined above) or O—C(=O)—$R^9$ (in which $R^9$ has the same meaning as defined above) can be obtained, for example, by dehydration condensation using a combination of polyalkylene glycol A and a polycarboxylic acid, or a carboxylic acid derivative of polyalkylene glycol A and a polyol. Dehydration condensation can be carried out by dehydration in the presence of an acid or base catalyst as in ordinary ester synthesis, or by condensing a corresponding alcohol compound and carboxylic acid using a condensing agent such as N,N'-dicyclohexylcarbodiimide in an appropriate solvent (e.g. dimethylformamide, dimethyl sulfoxide, acetonitrile, pyridine or methylene chloride). The desired compound can also be synthesized by reacting an acid halide with a corresponding alcohol compound in the above step.

The reaction conditions and purification conditions in each step are similar to those in the above processes.

Process 5-1

Among Compounds (Ie), those wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy, or substituted or unsubstituted aryloxycarbonyloxy can be obtained by synthesizing Compound (Ie) according to Process 5, and then combining the methods described in Process 1-1 to Process 1-9.

Process 6: Compounds wherein $X^1$ is $R^{6a}$—O—C(=O)—NH or $R^4$—NH—C(=O)—O

Compound (Ifa), i.e. Compound (I) wherein $X^1$ is $R^{6a}$—O—C(=O)—NH (in which $R^{6a}$ has the same meaning as defined above) can be produced, for example, in the following manner.

A crude product containing Compound (Ifa) can be obtained by reacting a commercially available polyamine or a polyamine prepared from a polyol by a combination of the above processes with at least 3 mol of a carbonate derivative of polyalkylene glycol A. The carbonate derivative of polyalkylene glycol A can be produced according to the method of Talia Miron, et al. [Bioconjugate Chem., Vol. 4, p. 568 (1993)]. As the carbonate derivative of polyalkylene glycol A, N-hydroxysuccinimidyl carbonate, p-nitrophenyl carbonate, imidazolylcarbonyloxy derivative, etc. can be used.

Compound (Ifb), i.e. Compound (I) wherein $X^1$ is $R^4$—NH—C(=O)—O (in which $R^4$ has the same meaning as defined above) can be produced, for example, in the following manner.

Compound (Ifb) can be obtained by reacting a carbonate derivative of a polyol with an amino derivative of polyalkylene glycol A in a manner similar to the above.

It is also possible to selectively form Compound (Ifa) or Compound (Ifb) by combining protection and deprotection of a functional group according to other processes.

The reaction conditions and purification conditions in each step are similar to those in the above processes.

Process 6-1

Among Compounds (If), those wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy, or substituted or unsubstituted aryloxycarbonyloxy can be prepared by synthesizing Compound (If) according to Process 6, and then combining the methods described in Process 1-1 to Process 1-9.

It is also possible to obtain a single- or double-chain compound by binding $R^1$-$M_n$-$X^1$ to L, and then obtain a compound having three or more chains by binding $R^1$-$M_n$-$X^1$ which is the same or different from the above to L through similar reaction. For example, a single- or double-chain compound is obtained by binding polyalkylene glycol to one or two functional groups in L by utilizing reaction selected from those shown in Processes 1 to 6. The content of the single- or double-chain compound formed can be controlled by changing the ratio of the polyalkylene glycol used in the reaction to the starting material for constructing the structure of L moiety, and thus it is possible to produce the single- or double-chain compound as a main component. The obtained single- or double-chain compound can be used in the next step at the purity as it is or after purifying it to a desired purity according to the number of branches of polyalkylene glycol or to a high purity by the method shown in Process 1.

A compound having three or more chains can be prepared by binding polyalkylene glycol which is the same or different from the above to the single- or double-chain compound obtained above according to the method selected from those shown in Processes 1 to 6. The third or further polyalkylene glycol may be subjected to reaction similar to that for obtaining the single- or double-chain compound, or may be subjected to a different reaction so as to have a different binding mode. For example, when a compound having two or more functional groups such as a hydroxyl group, amino and carboxy is used as a starting material for constructing the structure of L moiety, it is possible to first obtain a single- or double-chain compound wherein $X^1$ is O by the method shown in Process 1, and then subject the third or further polyalkylene glycol to reaction so that $X^1$ becomes $R^4$—NH—C(=O)—$R^5$ by the method shown in Process 4. As described above, a compound having three or more chains wherein plural polyalkylene glycols are bound to L in the same or different binding mode can be obtained by combining Processes 1 to 6. The molecular weights of polyalkylene glycols used in the respective reaction steps may be different, and a desired compound can readily be obtained by using polyalkylene glycols having different average molecular weights in the respective reactions for binding polyalkylene glycols to L.

In the reaction for introducing polyalkylene glycols to L, it is also possible to protect functional groups in L with appropriate protective groups with the exception of at least one functional group (e.g. in Process 1, at least one hydroxyl group) left unprotected, allow L to react with polyalkylene glycols for binding, and then remove the protective groups.

The branched polyalkylene glycols of the present invention other than the compounds specifically shown in the above processes can also be obtained according to processes similar to those described above.

As described above, the polyalkylene glycols used as starting materials in Processes 1 to 6 are commercially available, but can also be easily produced by various methods summarized by Samuel Zalipsky [Bioconjugate Chem., Vol. 6, p. 150 (1995)], etc.

The obtained branched polyalkylene glycols can be purified to a desired purity according to the number of branches by methods such as silica gel chromatography, reversed phase chromatography, hydrophobic chromatography, ion-exchange chromatography, gel filtration chromatography, recrystallization and extraction.

The resulting branched polyalkylene glycols can be bound to an amino acid side chain, the N-terminal amino group or the C-terminal carboxyl group of the above physiologically active polypeptide directly or through a spacer.

As the spacer, amino acids and peptides are preferably used, but other substances may also be used so long as they can bind to polyalkylene glycols. Suitable amino acids include natural amino acids such as lysine and cysteine, as well as ornithine, diaminopropionic acid, homocysteine and the like. Preferred is cysteine. Preferred peptides are those consisting of 2 to 10 amino acid residues. The spacers other than amino acids and peptides include glycerol, ethylene glycol and sugars. Suitable sugars include monosaccharides and disaccharides such as glucose, galactose, sorbose, galactosamine and lactose.

The spacer is bound to a side chain of the residue of lysine, cysteine, arginine, histidine, serine, threonine or the like in a physiologically active polypeptide molecule through an amide bond, a thioether bond, an ester bond, etc., to the C-terminal carboxyl group of the polypeptide through an amide bond or an ester bond, or to the N-terminal amino group of the polypeptide through an amide bond. The binding can be effected by ordinary peptide synthetic methods [Izumiya, et al., Peptide Gosei no Kiso to Jikken (Basis and Experiment of Peptide Synthesis) (1985), Maruzen] or recombinant DNA techniques.

It is preferred to introduce an amino acid, a peptide or the like as a spacer to the C-terminal carboxyl group of a physiologically active polypeptide simultaneously with the synthesis of the physiologically active polypeptide, but the spacer may be bound after the synthesis of the physiologically active polypeptide. It is also possible to activate the C-terminal carboxyl group or the like of the polypeptide in a chemical synthetic manner and then bind it to the spacer. Further, a spacer bound to polyalkylene glycol in advance may be bound to a physiologically active polypeptide by the method described above.

The physiologically active polypeptides used in the present invention include polypeptides, antibodies, and derivatives thereof. Examples of the polypeptides include enzymes such as asparaginase, glutaminase, arginase, uricase, superoxide dismutase, lactoferin, streptokinase, plasmin, adenosine deaminase, plasminogen activator and plasminogen; cytokines such as interleukin-1 to 18, interferon-α, interferon-β, interferon-γ, interferon-ω, interferon-τ, granulocyte-colony stimulating factor, thrombopoietin, erythropoietin, tumor necrosis factor, fibroblast growth factor-1 to 18, midkine, epidermal growth factor, osteogenic protein 1, stem cell factor, vascular endothelial growth factor, transforming growth factor and hepatocyte growth factor; hormones such as glucagon, parathyroid hormone and glucagon like peptide; klotho protein, angiopoietin, angiostatin, leptin, calcitonin, amylin, insulin like growth factor 1 and endostatin.

The antibodies used in the present invention can be obtained as polyclonal antibodies or monoclonal antibodies by using a known method [Antibodies—A Laboratory Manual, Cold Spring Harbor Laboratory (1988)].

The antibody used in the present invention may be either a polyclonal antibody or a monoclonal antibody, but a monoclonal antibody is preferred.

The monoclonal antibodies of the present invention include antibodies produced by hybridomas, humanized antibodies, and fragments thereof.

The humanized antibodies include human chimera antibodies and human CDR-grafted antibodies.

By "human chimera antibodies" is meant antibodies comprising the heavy-chain variable region (hereinafter, also referred to as HV or VH, the heavy chain being referred to as H chain and the variable region as V region) and the light-chain variable region (hereinafter, also referred to as LV or VL, the light chain being referred to as L chain) of an antibody derived from a non-human animal, and the heavy-chain constant region (hereinafter, also referred to as CH, the constant region being referred to as C region) and the light-chain constant region (hereinafter, also referred to as CL) of a human antibody. As the non-human animal, any animal can be used so far as hybridomas can be prepared from the animal. Suitable animals include mouse, rat, hamster and rabbit.

By "human CDR-grafted antibodies" is meant antibodies prepared by grafting the amino acid sequences of the CDR in the V regions of H chain and L chain of an antibody of a non-human animal into appropriate sites in the V regions of H chain and L chain of a human antibody.

The antibody fragments include Fab, Fab', F(ab')$_2$, single-chain antibodies, disulfide-stabilized V region fragments, and peptides comprising a complementarity determining region.

Fab is a fragment with a molecular weight of about 50,000 having antigen-binding activity constituted of about half of H chain (N-terminal side) and the full L chain, which is obtained by cleaving the peptide moiety above two disulfide bonds cross-linking two H chains in the hinge regions of IgG with papain.

Fab' is a fragment with a molecular weight of about 50,000 having antigen-binding activity, which is obtained by cleaving disulfide bonds of the hinge regions of the above F(ab')$_2$.

F(ab')$_2$ is a fragment with a molecular weight of about 100,000 having antigen-binding activity constituted of two Fab regions bound at the hinge regions, which is obtained by cleaving the part below two disulfide bonds in the hinge regions of IgG with trypsin.

The single-chain antibody (hereinafter also referred to as scFv) refers to a VH-P-VL or VL-P-VH polypeptide in which one VH and one VL are linked using an appropriate peptide linker (hereinafter referred to as P). The VH and VL contained in the scFv used in the present invention may be any of the monoclonal antibody and the human CDR-grafted antibody of the present invention.

The disulfide-stabilized V region fragment (hereinafter also referred to as dsFv) is a fragment in which polypeptides prepared by substituting one amino acid residue in each of VH and VL with a cysteine residue are linked via a disulfide bond. The amino acid residue to be substituted with a cysteine residue can be selected based on the prediction of the three-dimensional structure of antibody according to the method shown by Reiter, et al. [Protein Engineering, Vol. 7, p. 697 (1994)]. The VH and VL contained in the disulfide-stabilized antibody of the present invention may be any of the monoclonal antibody and the human CDR-grafted antibody.

The derivatives of the physiologically active polypeptides include amino acid-substituted derivatives, amino acid-deleted derivatives, sugar chain-added derivatives, sugar chain-deleted derivatives and partial peptides.

Among the physiologically active polypeptides and derivatives thereof described above, preferred examples include interferons such as interferon-β, interferon-α and interferon-γ, granulocyte-colony stimulating factor and superoxide dismutase.

These physiologically active polypeptides can be obtained not only by extraction from animal organs and tissues, but also by ordinary peptide synthesis and recombinant DNA techniques. Commercially available polypeptides can also be used.

The polypeptide used in the reaction may be a partially purified product or a product purified to a purity suitable for chemical modification by purification methods such as gel filtration chromatography, ion-exchange chromatography, hydrophobic chromatography, reversed phase chromatography and extraction.

The polypeptide is produced in a buffer such as a phosphate buffer, a borate buffer, an acetate buffer or a citrate buffer, water, an appropriate organic solvent such as N,N-dimethylformamide, dimethyl sulfoxide, dioxane or tetrahydrofuran, or a mixed solvent of such an organic solvent and an aqueous solution, and then used in chemical modification reaction.

The branched polyalkylene glycols of the present invention can also be used for site-specific covalent modification of polypeptides, more specifically and preferably, all natural or recombinant polypeptides having a free cysteine residue such as granulocyte-colony stimulating factor (G-CSF), erythropoietin, interferons and interleukins.

The physiologically active polypeptide modified with the branched polyalkylene glycol of the present invention is produced by reaction using the branched polyalkylene glycol in an amount of 1 to 1000 mol, preferably 1 to 50 mol per mol of a physiologically active polypeptide. The degree of modification of the physiologically active polypeptide with the branched polyalkylene glycol can be arbitrarily selected by controlling the molar ratio of the branched polyalkylene glycol to the physiologically active polypeptide, reaction temperature, pH, reaction time, etc. The solvent used in the reaction may be any of the solvents that do not interfere with the reaction, for example, a phosphate buffer, a borate buffer, a tris-hydrochloride buffer, an aqueous sodium hydrogencarbonate solution, a sodium acetate buffer, N,N-dimethylformamide, dimethyl sulfoxide, methanol, acetonitrile and dioxane. The temperature, pH and time of the reaction are not limited so long as the activity of the physiologically active polypeptide is not impaired under the conditions. For example, the reaction is preferably carried out at 0 to 50° C. at pH 4 to 10 for 10 minutes to 100 hours.

The physiologically active polypeptide modified with the branched polyalkylene glycol of the present invention can be purified by gel filtration, ion-exchange chromatography, reversed phase high performance liquid chromatography, affinity chromatography, ultrafiltration or the like in a usual manner. Confirmation of the polypeptide structure in the synthesized or purified physiologically active polypeptide or the physiologically active polypeptide modified with the branched polyalkylene glycol can be carried out by mass spectrometry, nuclear magnetic resonance (NMR) and amino acid composition analysis using an amino acid analyzer, and also by amino acid sequence analysis by use of a gas phase protein sequencer in which phenylthiohydantoin (PTH) amino acid obtained by Edman degradation is analyzed by reversed phase HPLC.

The chemically modified polypeptide of the present invention can be administered in the form of a pharmaceutical composition for human or animals, and the composition can be produced by ordinary methods for producing pharmaceuticals. The methods of administration include oral, intravenous, subcutaneous, submuscular, intraperitoneal and percutaneous administration and other acceptable methods, and a composition suitable for administration can be used. The composition may comprise generally employed additives such as an isotonizing agent, a buffer, an excipient, a pH regulator, a stalilizer, an antiseptic, a solubilizing agent, a wetting agent, an emulsifier, a lubricant, a sweetener, a coloring agent and an antioxidant.

Specific examples of Compounds (I) are shown in Tables 1 and 2.

The following are supplementary explanations of the structure of the compounds shown in Table 1.

1) In Compound 5TRC(3UA) obtained in Example 1, the carboxyl group corresponding to $(X^2—X^3—R^2)$ binds to the methylene group of —NHCH$_2$—. CH$_3$—(OCH$_2$CH$_2$)$_n$—NH(C=O)— corresponding to [CH$_3$—(OCH$_2$CH$_2$)$_n$—X$^1$] binds to the methyleneoxy groups (—CH$_2$O—).

2) In Compound 5SKA(3UA) obtained in Example 2, the carboxyl group corresponding to $(X^2—X^3—R^2)$ binds to the 1-position of the cyclohexene ring. CH$_3$—(OCH$_2$CH$_2$)$_n$—NH(C=O)—corresponding to [CH$_3$—(OCH$_2$CH$_2$)$_n$—X$^1$] binds to the oxygen atoms at the 3-, 4- and 5-positions of the cyclohexene ring.

3) In Compound 5QNA(4UA) obtained in Example 3, the carboxyl group corresponding to $(X^2—X^3—R^2)$ binds to the 1-position of the cyclohexane ring, and the carboxyl group sterically exists in the upward direction from the plane of the figure. CH$_3$—(OCH$_2$CH$_2$)$_n$—NH(C=O)—O— binding to the 1-position sterically exists in the downward direction from the plane of the figure. CH$_3$—(OCH$_2$CH$_2$)—NH(C=O)—corresponding to [CH$_3$—(OCH$_2$CH$_2$)$_n$—X$^1$] binds to the oxygen atoms at the 1-, 3-, 4- and 5-positions of the cyclohexane ring.

4) In Compound 5PET(3UA) obtained in Example 4, —O—(C=O)—NH(CH$_2$)$_3$COOH corresponding to $(X^2—X^3—R^2)$ binds to the methylene group (—CH$_2$—). CH$_3$—(OCH$_2$CH$_2$)$_n$—CH$_2$—NH(C=O)— corresponding to [CH$_3$—(OCH$_2$CH$_2$)—X$^1$] binds to the methyleneoxy groups (—CH$_2$O—).

5) In Compound 5PET(3UM) obtained in Example 5, the 3-maleimidopropylaminocarbonyloxy group corresponding to $(X^2—X^3—R^2)$ binds to the methylene group (—CH$_2$—). CH$_3$—(OCH$_2$CH$_2$)$_n$—CH$_2$—NH(C=O)—corresponding to [CH$_3$—(OCH$_2$CH$_2$)$_n$—X$^1$] binds to the methyleneoxy groups (—CH$_2$O—).

6) In Compound 5PET(3UU) obtained in Example 6, the maleimidooxycarbonyloxy group corresponding to $(X^2—X^3—R^2)$ binds to the methylene group (—CH$_2$—). CH$_3$—(OCH$_2$CH$_2$)$_n$—CH$_2$—NH(C=O)— corresponding to [CH₃—(OCH₂CH₂)ₙ—X¹] binds to the methyleneoxy groups (—CH₂O—).

7) In Compound 5PET(3URa) obtained in Example 7, —O—(C=O)—NH(CH₂)₃CHO corresponding to (X²—X³—R²) binds to the methylene group (—CH₂—). CH₃—(OCH₂CH₂)ₙ—CH₂—NH(C=O)— corresponding to [CH₃—(OCH₂CH₂)ₙ—X¹] binds to the methyleneoxy groups (—CH₂O—).

8) In Compound 5SUG(4UA) obtained in Example 8, the carboxyl group —O—(C=O) corresponding to (X²—X³—R²) binds to the oxymethylene group (—OCH₂—) at the 1-position. CH₃—(OCH₂CH₂)ₙ—CH₂—NH(C=O)— corresponding to [CH₃—(OCH₂CH₂)ₙ—X¹] binds to the oxygen atoms at the 2-, 3- and 4-positions and the methyleneoxy group at the 5-position.

TABLE 1

$$[CH_3-(OCH_2CH_2)_n-X^1]_m-L-(X^2-X^3-R^2)_q \quad (I)$$

| Example No. Abbrev. | X¹ | m | L | q | X²—X³—R² |
|---|---|---|---|---|---|
| 1 5TRC(3UA) | —NH—C(=O)— | 3 | [pentaerythritol-like core with N—CH₂—] | 1 | —C(=O)—OH |
| 2 5SKA(3UA) | —NH—C(=O)— | 3 | [cyclohexene ring with O at 3,4,5 positions, methyl at 1] | 1 | —C(=O)—OH |
| 3 5QNA(4UA) | —NH—C(=O)— | 4 | [cyclohexane ring with O at 3,4,5 positions; OH and methyl at 1] | 1 | —C(=O)—OH |
| 4 5PET(3UA) | —CH₂—NH—C(=O)— | 3 | [pentaerythritol core] | 1 | —O—C(=O)—NH—(CH₂)₃—COOH |
| 5 5PET(3UM) | —CH₂—NH—C(=O)— | 3 | [pentaerythritol core] | 1 | —O—C(=O)—NH—(CH₂)₃—maleimide |
| 6 5PET(3UU) | —CH₂—NH—C(=O)— | 3 | [pentaerythritol core] | 1 | —O—C(=O)—O—N-succinimidyl |
| 7 5PET(3URa) | —CH₂—NH—C(=O)— | 3 | [pentaerythritol core] | 1 | —O—C(=O)—NH—(CH₂)₃—CHO |
| 8 5SUG(4UA) | —CH₂—NH—C(=O)— | 4 | [pyranose sugar ring with O at 2,3,4,5 positions] | 1 | —C(=O)—OH |

TABLE 2

$[CH_3—(OCH_2CH_2)_n—X^1]_m—L—(X^2—X^3—R^2)_q$ (I)

| Example No.<br>Abbrev. | Structure of Compound (I) |
|---|---|
| 3<br>5QNA(3UA) | 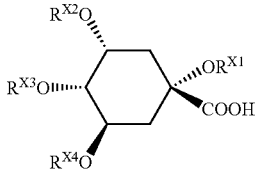<br>One of $R^{X1}$, $R^{X2}$, $R^{X3}$ and $R^{X4}$ is a hydrogen atom and the other three are $CH_3—(OCH_2CH_2)_n—NH—C(=O)—$. |
| 8<br>5SUG(3UA) | 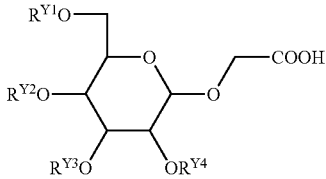<br>One of $R^{Y1}$, $R^{Y2}$, $R^{Y3}$ and $R^{Y4}$ is a hydrogen atom and the other three are $CH_3—(OCH_2OCH_2)_n—CH_2—NH—C(=O)—$. |

BEST MODES FOR CARRYING OUT THE INVENTION

Figure 1:
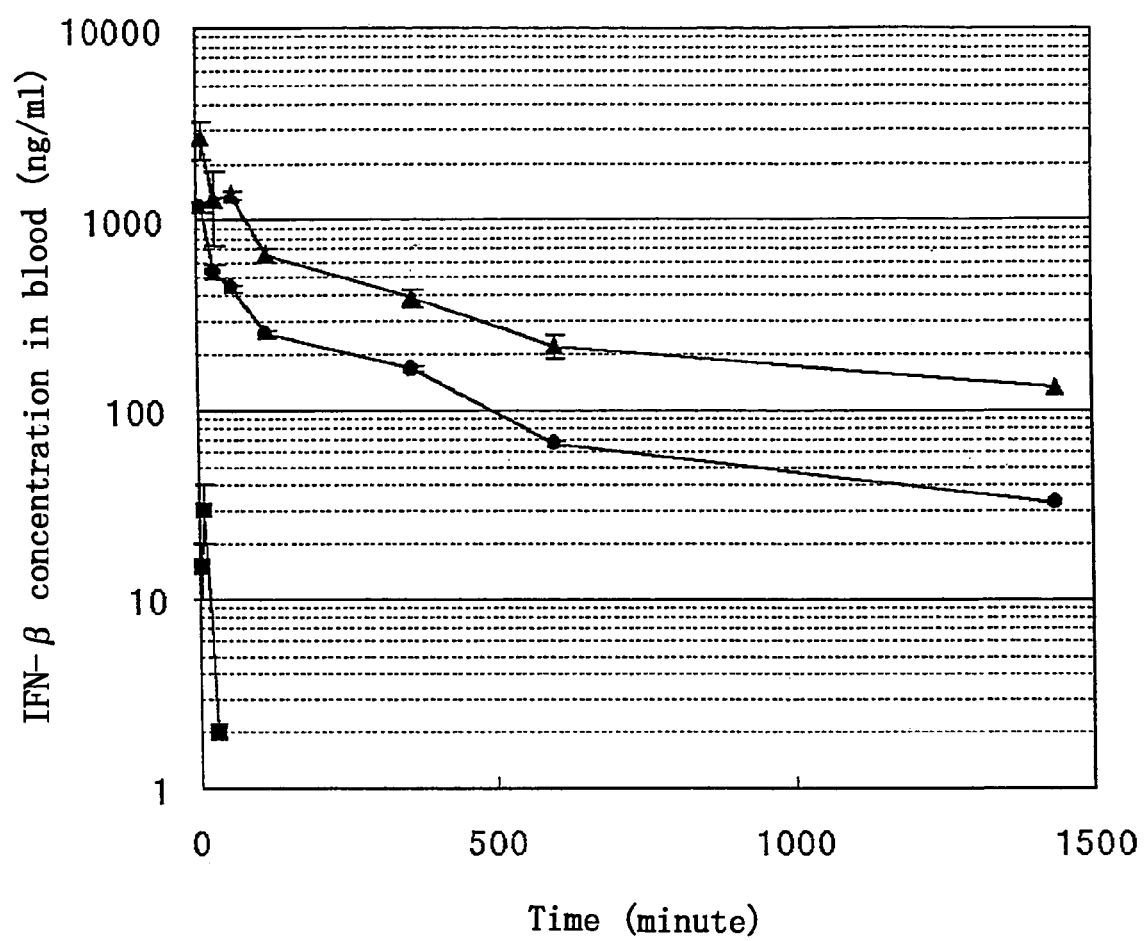
FIG. 1 shows the blood half-life prolonging effect of chemically modified recombinant human interferon-β when intravenously injected into mice.
- ■ -: change in the concentration of unmodified rhIFN-β in blood
- ▲ -: change in the concentration of 5TRC(3UA)-rhIFN-β in blood
- ● -: change in the concentration of PEG$_2$Lys-rhIFN-β in blood

The present invention is specifically described by the following examples, which are not to be construed as limiting the scope of the invention. The abbreviations in the examples mean the following unless otherwise specified. The abbreviations for amino acids and their protective groups used herein follow the recommendations by IUPAC-IUB Commission on Biochemical Nomenclature [Eur. J. Biochem., Vol. 138, p. 9 (1984)].

HPLC: high performance liquid chromatography
RI: refractive index
NMR: nuclear magnetic resonance
ELISA: enzyme-linked immunosorbent assay
SDS-PAGE: sodium dodecyl sulfate-polyacrylamide gel electrophoresis
PEG: poly(ethylene glycol)
mPEG: monomethoxy poly(ethylene glycol)
IFN: interferon
hIFN: human interferon
rhIFN: recombinant human interferon
G-CSF: granulocyte-colony stimulating factor
rhG-CSF: recombinant human granulocyte-colony stimulating factor
SOD: superoxide dismutase
bSOD: bovine superoxide dismutase
hSOD: human superoxide dismutase
DSC: N,N'-disuccinimidyl carbonate
TEA: triethylamine
DMF: N,N-dimethylformamide
DMSO: dimethyl sulfoxide
NHS: N-hydroxysuccinimide
Ts: p-toluenesulfonyl
TsCl: p-toluenesulfonyl chloride
DMAP: dimethylaminopyridine
PyBOP: benzotriazol-1-yloxy-tripyrrolidinophosphonium hexafluorophosphate
HOBt: N-hydroxybenzotriazole
DCC: N,N'-dicyclohexylcarbodiimide
LAH: lithium aluminium hydride
NMM: N-methylmorpholine
TFA: trifluoroacetic acid
CDI: N,N'-carbonyldiimidazole

EXAMPLE 1

Synthesis of 5 kDa Three-chain Branched Polyethylene Glycol-tricine Derivative

Abbreviation: 5TRC(3UA)

In 0.5 ml of DMF were dissolved 0.5 mg (2.8 μmol) of tricine (N-[Tris(hydroxymethyl)methyl]glycine, Nacalai Tesque, Inc.) and 50 mg (10.0 μmol) of PEG-NCO (Shearwater Polymers, Inc., average molecular weight: 5,000, structure: $CH_3(OCH_2CH_2)_n$—N=C=O) in a stream of argon. To the solution were added 1.4 μl (10.0 μmol) of TEA and then ca. 1 mg of copper chloride, followed by stirring at room temperature for 5 hours. To the mixture were further added 10 mg of PEG-NCO and 1 μl of TEA, followed by stirring for 2 hours. Then, 15 mg of PEG-NCO was added and the mixture was stirred a whole day and night at room temperature.

After addition of 50 ml of 0.1 mol/l hydrochloric acid, the mixture was extracted with 50 ml of chloroform. The chloroform layer was dried over anhydrous sodium sulfate and the solvent was removed under reduced pressure. The residue was dissolved in a small amount of methylene chloride and the solution was added dropwise to diethyl ether. The formed white precipitate was recovered by filtration to obtain 15 mg of a crude product containing the desired compound (yield: 20%). This product was purified by DEAE Sepharose F.F. column (Amersham-Pharmacia Biotech). Elution was carried out with a 1 mol/l aqueous solution of sodium chloride, and the eluate was extracted with chloroform under acidic conditions, followed by drying over anhydrous sodium sulfate. Thereafter, the solvent was removed under reduced pressure to obtain 6.0 mg of the desired compound (yield: 8.0%).

<Gel Filtration HPLC Analysis>

The product was analyzed using TSKgelG2000SW$_{XL}$ column (7.8×300 mm, Tosoh Corporation) under the following conditions.

Mobile phase: 150 mmol/l sodium chloride, 20 mmol/l sodium acetate buffer (pH 4.5)
Flow rate: 0.7 ml/minute
Detection: R$^1$
Retention time: 11.5 minutes <$^1$H-NMR analysis (300 MHz, in CDCl$_3$)> δ (ppm): 3.38(s, 9H), 3.64(s, 12nH), 4.10(s, 6H), 5.43(br, 3H)

EXAMPLE 2

Synthesis of 5 kDa Three-chain Branched Polyethylene Glycol-shikimic Acid Derivative Abbreviation: 5SKA(3UA)

In 250 μl of DMF was dissolved 3.2 mg of shikimic acid, and 15 μl of triethylamine and a catalytic amount of copper chloride were added thereto. To the mixture was added 300 mg of PEG-NCO (Shearwater Polymers, Inc., average molecular weight: 5,000, structure: CH$_3$(OCH$_2$CH$_2$)$_n$—N=C=O), followed by stirring at room temperature for one hour. The reaction mixture was added dropwise to diethyl ether, and the formed precipitate was recovered by filtration and dried under reduced pressure to obtain 270 mg (89%) of a crude desired product.

The product was purified using DEAE Sepharose F.F. column (Amersham-Pharmacia Biotech) in a manner similar to that in Example 1. The desired fraction was extracted with chloroform and the solvent was removed under reduced pressure to obtain 18 mg of the desired compound (yield: 6%).

<Gel Filtration HPLC Analysis>

Measurement was carried out using TSKgelG2000SW$_{XL}$ column under conditions similar to those in Example 1.
Retention time: 11.7 minutes <$^1$H-NMR analysis (300 MHz, in CDCl$_3$)> δ(ppm): 3.38 (s, 9H), 3.64(s, 12nH), 5.1-6.6(m, 4H)

EXAMPLE 3

Synthesis of 5 kDa Three- and Four-chain Branched Polyethylene Glycol-quinic Acid Derivatives Abbreviation: 5QNA(3UA), 5QNA(4UA)

In 250 μl of DMF was dissolved 3 mg of quinic acid ((1R, 3R, 4R, 5R)-(−)-quinic acid), and 17 μl of triethylamine and a catalytic amount of copper chloride were added thereto. To the mixture was added 344 mg of PEG-NCO (Shearwater Polymers, Inc.), followed by stirring at room temperature for one hour. The reaction mixture was added dropwise to diethyl ether, and the formed precipitate was recovered by filtration and dried under reduced pressure to obtain 306 mg (88%) of a crude desired product. The product was purified using DEAE Sepharose F.F. column (Amersham-Pharmacia Biotech) in a manner similar to that in Example 1. The desired fraction was extracted with chloroform, and the solvent was removed under reduced pressure to obtain the following compounds.

TABLE 3

| Compound abbrev. | Number of PEG bound | Amount of product | Yield | Retention time in gel filtration HPLC* |
|---|---|---|---|---|
| 5QNA (3UA) | 3 | 24 mg | 10.2% | 11.7 minutes |
| 5QNA (4UA) | 4 | 17 mg | 5.4% | 11.1 minutes |

*Measurement was carried out using TSKgelG2000SW$_{XL}$ column under conditions similar to those in Example 1.

<$^1$H-NMR analysis (300 MHz, in CDCl$_3$)> Compound 5QNA(3UA): δ (ppm): 3.38(s, 9H), 3.64(s, 12nH), 4.8-5.7 (m, 3H)

Compound 5QNA(4UA): δ (ppm): 3.38(s, 12H), 3.64 (s, 16nH) 4.8-5.7(m, 3H)

EXAMPLE 4

Synthesis of 5 kDa Three-chain Branched Polyethylene Glycol-pentaerythritol Derivative Abbreviation: 5PET(3UA)

In 5 ml of DMF were dissolved 136 mg of pentaerythritol and 122 mg of DMAP in a stream of argon, and 778 mg of CDI was added thereto. The mixture was stirred a whole day and night at 0° C. to room temperature. In 10 ml of DMF was dissolved 5.0 g of mPEG-NH$_2$ (NOF Corporation, average molecular weight: 5,000, structure: CH$_3$(OCH$_2$CH$_2$)$_n$—CH$_2$—NH$_2$), and 1.25 ml of the above reaction mixture was added thereto, followed by stirring at room temperature for 2 hours. A solution of 2.6 g of γ-aminobutyric acid in 100 ml of 0.1 mol/l borate buffer (pH 10) was ice-cooled, and the reaction mixture was poured into this solution. After stirring at 0° C. for 2 hours and at room temperature for 4 hours, the mixture was made acidic with hydrochloric acid and then extracted with chloroform. The solvent was removed under reduced pressure to obtain 4.2 g of a residue (84.6%). The residue (3.8 g) was purified using DEAE Sepharose F.F. column (1000 ml, Amersham-Pharmacia Biotech) in a manner similar to that in Example 1 to obtain 254 mg of the desired compound (yield: 6.7%).

<Gel Filtration HPLC Analysis>

Measurement was carried out using TSKgelG2000SW$_{XL}$ column under conditions similar to those in Example 1.
Retention time: 11.4 minutes <$^1$H-NMR analysis (300 MHz, in CDCl$_3$)>δ (ppm): 5.44 (brt, J=5.0 Hz, 3H), 5.25(br, 1H), 4.09(brs, 8H), 3.65(s, 12nH), 3.29(s, 9H), 3.26(m, 8H), 2.37(t, J=6.8 Hz, 2H), 1.80(brm, 2H), 1.77(m, 6H)

EXAMPLE 5

Synthesis of 5 kDa Three-chain Branched Polyethylene Glycol-pentaerythritol Derivative Abbreviation: 5PET(3UM)

In 5 ml of DMF were dissolved 136 mg of pentaerythritol and 122 mg of DMAP, and 778 mg of CDI was added thereto. The mixture was stirred a whole day and night at 0° C. to room temperature in a stream of argon. In 2 ml of DMF was dissolved 1.0 g of mPEG-NH$_2$ (NOF Corporation, average molecular weight: 5,000), and 0.25 ml of the above reaction mixture was added thereto, followed by stirring at room temperature for 2 hours. Then, 187 µl of propylenediamine was added thereto, and the mixture was stirred at room temperature for 2 hours, followed by addition of diethyl ether. The formed white precipitate was recovered and dried under reduced pressure to obtain 975 mg of a residue (yield: 97.5%). The residue was purified using SP Sepharose F.F. column (100 ml, Amersham-Pharmacia Biotech), and the fraction eluted with 0.2 to 0.4 mmol/l NaCl was extracted with chloroform to obtain 110 mg of a white powder (yield: 11.3%).

Subsequently, 100 mg of the white powder was dissolved in 0.5 ml of a saturated aqueous solution of sodium hydrogencarbonate, and 2.3 mg of ethoxycarbonyl maleimide was added thereto at 0° C., followed by stirring at 0° C. for 10 minutes. After addition of 1.5 ml of water, the mixture was stirred at room temperature for 15 minutes and then extracted with chloroform. The chloroform layer was concentrated under reduced pressure and added dropwise to diethyl ether. The formed white precipitate was dried under reduced pressure to obtain 35 mg of the desired compound (yield: 35%).

<Gel Filtration HPLC Analysis>

Measurement was carried out using TSKgelG2000SW$_{XL}$ column under conditions similar to those in Example 1. Retention time: 11.3 minutes <$^1$H-NMR analysis (300 MHz, in CDCl$_3$)> δ (ppm): 6.73(s, 2H), 5.33(br, 3H), 4.08(brs, 8H), 3.64(s, 12nH), 3.36(s, 9H), 3.25(m, 6H), 3.11(m, 2H), 1.77(m, 8H)

EXAMPLE 6

Synthesis of Three-chain Branched Polyethylene Glycol-pentaerythritol Derivative Abbreviation: 5PET(3UU)

In 5 ml of DMF were dissolved 136 mg of pentaerythritol and 122 mg of DMAP, and 681 mg of CDI was added thereto. The mixture was stirred a whole day and night at 0° C. to room temperature in a stream of argon. In 2 ml of DMF was dissolved 1.0 g of mPEG-NH$_2$ (NOF Corporation, average molecular weight: 5,000), and 286 µl of the above reaction mixture was added thereto, followed by stirring at room temperature for 2 hours. The resulting reaction mixture was added dropwise to diethyl ether, and the formed white precipitate was recovered and dried under reduced pressure to obtain 1 g of a residue (yield: 100%).

The residue was purified using TSKgelODS-120T column (30 mm×250 mm, Tosoh Corporation). As an eluent, 0 to 90% aqueous acetonitrile solution containing 0.1% TFA was used. The fraction containing three-chain PEG was concentrated under reduced pressure and extracted with chloroform, and the solvent was removed under reduced pressure to obtain 165 mg of a residue (yield: 16.5%).

The obtained white powder (80 mg) was dissolved in 1 ml of methylene chloride, and 4.1 mg of DSC and 2.1 mg of DMAP were added thereto, followed by stirring at room temperature for 6 hours in a stream of argon. The reaction mixture was added dropwise to diethyl ether, and the formed white precipitate was dried under reduced pressure to obtain 63 mg of the desired compound (yield: 78.8%).

<Gel Filtration HPLC Analysis>

Measurement was carried out using TSKgelG2000SW$_{XL}$ column under conditions similar to those in Example 1. Retention time: 10.7 minutes <$^1$H-NMR analysis (300 MHz, in CDCl$_3$)> δ (ppm): 5.49(br, 3H), 4.11(brs, 8H), 3.64(s, 12nH), 3.38(s, 9H), 3.25(m, 6H), 2.87(s, 4H), 1.78(m, 8H)

EXAMPLE 7

Synthesis of Three-chain Branched Polyethylene Glycol-pentaerythritol Derivative Abbreviation: 5PET(3URa)

In 5 ml of DMF were dissolved 136 mg of pentaerythritol and 122 mg of DMAP, and 681 mg of CDI was added thereto. The mixture was stirred a whole day and night at 0° C. to room temperature in a stream of argon. In 2 ml of DMF was dissolved 1.0 g of mPEG-NH$_2$ (NOF Corporation, average molecular weight: 5,000), and 286 µl of the above reaction mixture was added thereto, followed by stirring at room temperature for 2 hours. The resulting reaction mixture was added dropwise to diethyl ether, and the formed white precipitate was recovered and dried under reduced pressure to obtain 950 mg of a residue (yield: 95%). The residue was purified using TSKgelODS-120T column (30 mm×250 mm, Tosoh Corporation). As an eluent, 0 to 90% aqueous acetonitrile solution containing 0.1% TFA was used. The fraction containing three-chain PEG was concentrated under reduced pressure and extracted with chloroform, and the solvent was removed under reduced pressure to obtain 300 mg of a residue (yield: 31.6%).

The obtained residue (white powder, 300 mg) was dissolved in 1 ml of methylene chloride, and 15.4 mg of DSC and 7.3 mg of DMAP were added thereto, followed by stirring at room temperature for 6 hours in a stream of argon. The reaction mixture was added dropwise to diethyl ether, and the formed white precipitate was dried under reduced pressure. The resulting dried product was dissolved in 1 ml of methylene chloride, and 3.5 µl of 4-aminobutyraldehyde diethylacetal was added thereto, followed by stirring at room temperature for 2 hours. The reaction mixture was added dropwise to diethyl ether, and the formed white precipitate was dried under reduced pressure to obtain 250 mg of a residue (yield: 83.3%).

The obtained residue (100 mg) was dissolved in methylene chloride containing 10% TFA, and the solution was allowed to stand at 0° C. for one hour. Then, the solution was added dropwise to diethyl ether, and the formed white precipitate was dried under reduced pressure to obtain 40 mg of the desired compound (yield: 40.0%).

<Gel Filtration HPLC Analysis>

Measurement was carried out using TSKgelG2000SW$_{XL}$ column under conditions similar to those in Example 1. Retention time: 10.6 minutes

EXAMPLE 8

Synthesis of Three- and Four-chain Branched Polyethylene Glycol-carbohydrate Derivatives Abbreviation: 5SUG(3UA), 5SUG(4UA)

In 80 ml of DMF was dissolved 5.18 g of α-D-glucose pentaacetate, and 2.37 g of hydrazine acetate was added thereto, followed by stirring at room temperature for 1.5 hours. The reaction mixture was extracted with ethyl acetate, and the ethyl acetate layer was washed with water and a saturated aqueous solution of sodium chloride, and then dried over anhydrous sodium sulfate. The solution was concentrated under reduced pressure to obtain 4.0 g of α-D-glucopyranose-2,3,4,6-tetraacetate (yield: 87%).

<$^1$H-NMR analysis (300 MHz, in CDCl$_3$)> δ (ppm): 2.02(s, 3H), 2.03(s, 3H), 2.08(s, 3H), 2.10(s, 3H), 4.14(m, 1H), 4.27(m, 2H), 4.91(m, 1H), 5.09(t, J=9.7 Hz, 1H), 5.47(d, J=3.7 Hz, 1H), 5.55(t, J=9.8 Hz, 1H)

The above compound (850 mg) was dissolved in 15 ml of methylene chloride, and 4.8 ml of trichloroacetonitrile and 365 ml of DBU (1,8-diazabicyclo[5.4.0]undec-7-ene) were added thereto at 0° C., followed by stirring at 0° C. for one hour and at room temperature for 15 minutes. The resulting solution was concentrated under reduced pressure and then purified using a silica gel column to obtain 635 mg of α-D-glucopyranose-2,3,4,6-tetraacetate-1-(2,2,2-trichloroethanimidate) (yield: 53%).

<$^1$H-NMR analysis (CDCl$_3$, 300 MHz)> δ (ppm): 2.02(s, 3H), 2.04(s, 3H), 2.06(s, 3H), 2.08(s, 3H), 4.13(m, 1H), 4.21(m, 1H), 4.28(m, 1H), 5.13(m, 1H), 5.19(t, J=9.8 Hz, 1H), 5.57(t, J=9.9 Hz, 1H), 6.56(d, J=3.7 Hz, 1H), 8.71(s, 1H)

The above compound (693 mg) and 109 μl of methyl glycolate were dissolved in dehydrated methylene chloride, and 1.62 g of molecular sieves 4A was added thereto, followed by stirring at room temperature for 4 hours in a stream of argon. The reaction mixture was cooled to 0 to 5° C., and 163 μl of a mixed solution of trimethylsilyl trifluoromethanesulfonate and dehydrated methylene chloride (2:1) was added thereto, followed by stirring at 0 to 5° C. for 19 hours. After addition of 77 μl of triethylamine, the mixture was filtered through Celite. The resulting solution was concentrated under reduced pressure and then purified using a silica gel column to obtain 162 mg of [(2,3,4,6-tetra-O-acetyl-β-D-glucopyranosyl)oxy] acetic acid methyl ester (yield: 27%).

<$^1$H-NMR analysis (CDCl$_3$, 300 MHz)> δ (ppm): 2.01(s, 3H), 2.03(s, 3H), 2.09(s, 3H), 2.10(s, 3H), 3.70(m, 1H), 3.75(s, 3H), 4.14(m, 1H), 4.26(m, 1H), 4.29(s, 2H), 4.67(d, J=7.8 Hz, 1H), 5.05(m, 1H), 5.09(t, J=10.8 Hz, 1H), 5.25(t, J=9.5 Hz, 1H)

The above compound (162 mg) was dissolved in 1 ml of methanol, and Amberlyst was added thereto. Then, 9.4 μl of a 28% solution of sodium methoxide in methanol was added, and the mixture was stirred at room temperature for 3 hours. After filtration through Celite, the filtrate was concentrated under reduced pressure to obtain 80 mg of [(β-D-glucopyranosyl)oxy] acetic acid methyl ester (yield: 82%).

<$^1$H-NMR analysis (D$_2$O, 300 MHz)> δ (ppm): 3.39(s, 2H), 3.40(m, 2H), 3.69(m, 1H), 3.75(s, 3H), 3.86(m, 1H), 4.06(m, 1H), 4.26(m, 1H), 4.44(m, 1H) <Mass spectrum (FAB-MS)> Found: [M+H]=253 Calcd.: C$_9$H$_{16}$O$_8$=252

The above compound (2 mg) was dissolved in 100 μl of DMF, and 7 μl of triethylamine and a catalytic amount of CuCl were added thereto. To the mixture was added 160 mg of mPEG-NCO, and the mixture was stirred at room temperature for 2 hours. Then, 80 mg of mPEG-NCO was added, followed by further stirring for 3 hours. The resulting solution was added dropwise to diethyl ether, and the formed white precipitate was recovered by filtration and dried under reduced pressure. The obtained white solid (200 mg) was dissolved in 2 ml of 1 mol/l aqueous solution of potassium carbonate, followed by stirring at room temperature for 4 hours. To the solution were added chloroform and 0.1 mol/l hydrochloric acid, and the mixture was extracted with chloroform. After the extract was dried over anhydrous sodium sulfate, the solvent was removed under reduced pressure, and the residue was dried under reduced pressure to obtain 195 mg of a white solid. This product was purified using DEAE Sepharose F.F. column (20 ml, Amersham-Pharmacia Biotech) to obtain the compounds shown below.

TABLE 4

| Compound abbrev. | Number of PEG bound | Amount of product | Yield | Retention time in gel filtration HPLC* |
|---|---|---|---|---|
| 5SUG (3UA) | 3 | 6mg | 5.0% | 10.8 minutes |
| 5SUG (4UA) | 4 | 12mg | 7.6% | 10.4 minutes |

*Measurement was carried out using TSKgelG2000SW$_{XL}$ column under conditions similar to those in Example 1.

<$^1$H-NMR analysis (300 MHz, in CDCl$_3$)> Compound 5SUG(3UA): δ (ppm): 3.38 (s, 9H), 3.64(t, 12nH) 4.1-5.6 (m, 7H) Compound 5SUG(4UA): δ (ppm): 3.38(s, 12H), 3.64(t, 16nH), 4.1-5.6(m, 7H)

EXAMPLE 9

Preparation of Recombinant Human Interferon-β Modified with 5 KDa Three-chain Branched Polyethylene Glycol Abbreviation: 5TRC(3UA)-rhIFN-β

To 5 mg (0.33 μmol) of the compound of Example 1 (5TRC(3UA)) were added 50 μl (0.66 μmol) of 1.5 mg/ml solution of NHS in methylene chloride and 100 μl (0.66μmol) of 1.4 mg/ml solution of DCC in methylene chloride, followed by stirring in a stream of argon under ice-cooling for 30 minutes and at room temperature for 2 hours. After addition of diethyl ether, the formed precipitate was dried under reduced pressure to obtain 3.5 mg (yield: 70%) of NHS ester.

To 150 μl of a 0.9 mg/ml solution of rhIFN-β obtained in Reference Example 4 in 20 mmol/l phosphate buffer containing ethylene glycol and sodium chloride was added 33.4 mg (34 mol per mol of protein) of the modifying reagent activated above (NHS ester), and the mixture was subjected to reaction by standing a whole day and night at 4° C. The reaction mixture was applied to a gel filtration column Sephadex G-25 (Amersham-Pharmacia Biotech) and subjected to buffer exchange with 20 mmol/l phosphate buffer (pH 6.0) containing ethylene glycol, followed by purification using CM Sepharose F.F. column (0.5 ml, Amersham-Pharmacia Biotech). After the reaction mixture was charged, the column was washed with 5 ml of the same buffer, and elution was carried out with the buffer containing sodium chloride. The fraction containing the desired substance was recovered to obtain 0.40 ml of the desired substance (0.091 mg/ml) (yield: 27.0%).

<Electrophoresis>

SDS-PAGE was carried out in the presence of 2-mercaptoethanol under the following conditions to confirm the bands of 1 to 3 molecules-bound substances.

Gel: PAGEL SPG 520L (Atto Corporation)

Staining: FAST STAIN™

Molecular weight marker: Low Molecular Weight Standard (Bio-Rad)

<Gel Filtration HPLC Analysis>

Analysis was carried out using two TSKgelG4000SW$_{XL}$ columns under the following conditions.

Mobile phase: 150 mmol/l sodium chloride, 20 mmol/l sodium acetate buffer (pH 4.5)
Flow rate: 0.5 ml/minute
Detection: UV 280 nm
Separation column: TSKgelG4000SW$_{XL}$ (7.8×300 mm×2, Tosoh Corporation)
Retention time: 42.0 minutes (1 molecule-bound substance)
44.1 minutes (2 molecules-bound substance)

EXAMPLE 10

Preparation of Recombinant Human Interferon-β Modified with 5 kDa Three-chain Branched Polyethylene Glycol Abbreviation: 5SKA(3UA)-rhIFN-β

In 100 μl of methylene chloride was dissolved 16 mg (1.1 μmol) of the compound of Example 2 (5SKA(3UA)), and 272 μg of DCC and 152 μg of NHS were added thereto, followed by stirring under ice-cooling for one hour and at room temperature for one hour. The mixture was added dropwise to diethyl ether, and the formed white precipitate was dried under reduced pressure to obtain 14.5 mg of NHS ester of the compound of Example 2 (yield: 91%).

To 100 μl of a 1.2 mg/ml solution of rhIFN-β obtained in Reference Example 4 in 20 mmol/l phosphate buffer containing ethylene glycol and sodium chloride was added 8.6 mg (100 mol per mol of protein) of the NHS ester obtained above, and the mixture was subjected to reaction by standing a whole day and night at 4° C. The reaction mixture was applied to a gel filtration column Sephadex G-25 (Amersham-Pharmacia Biotech) and subjected to buffer exchange with 20 mmol/l phosphate buffer (pH 6.0) containing ethylene glycol, followed by purification using CM Sepharose F.F. column (0.6 ml, Amersham-Pharmacia Biotech). After the reaction mixture was charged, the column was washed with 3 ml of the same buffer, and elution was carried out with the buffer containing sodium chloride. The fraction containing the desired substance was recovered to obtain 80 μl of the desired substance (47 μg/ml) (yield: 3.3%).

<Electrophoresis>
SDS-PAGE was carried out in the presence of 2-mercaptoethanol in a manner similar to Example 9 to confirm the band of 1 molecule-bound substance.

<Gel Filtration HPLC Analysis>
Analysis was carried out using two TSKgelG4000SW$_{XL}$ columns in a manner similar to Example 9.
Retention time: 41.7 minutes (1 molecule-bound substance)

EXAMPLE 11

Preparation of Recombinant Human Interferon-β Modified with 5 kDa Three-Chain Branched Polyethylene Glycol Abbreviation: 5PET(3UU)-rhIFN-β

To 0.5 ml of a 1.2 mg/ml solution of rhIFN-β obtained in Reference Example 4 in 20 mmol/l phosphate buffer (pH 7.8) containing ethylene glycol and sodium chloride was added 4.5 mg (10 mol per mol of protein) of 5PET(3UU) obtained in Example 6, and the mixture was subjected to reaction a whole day and night at 4° C. The reaction mixture (0.5 ml) was applied to Sephadex G-25 column (Amersham-Pharmacia Biotech) and subjected to buffer exchange with 20 mmol/l phosphate buffer (pH 6) containing ethylene glycol. The mixture was passed through CM-Sepharose F.F. column (0.8 ml, Amersham-Pharmacia Biotech), followed by washing with 4.0 ml of 20 mmol/l phosphate buffer (pH 6) containing ethylene glycol. Elution was carried out with the same buffer containing 0.1 to 0.5 mol/l sodium chloride, and the desired fractions were combined and then concentrated to obtain 0.36 ml of a solution containing the desired substance (0.67 mg/ml) (yield: 40%).

<Electrophoresis>
SDS-PAGE was carried out in the presence of 2-mercaptoethanol in a manner similar to Example 9 to confirm the bands of 1 to 3 molecules-bound substances.

<Gel Filtration HPLC Analysis>
Analysis was carried out using two TSKgelG4000SW$_{XL}$ columns in a manner similar to Example 9.
Retention time: 41.1 minutes (1 molecule-bound substance)
38.2 minutes (2 molecules-bound substance)

EXAMPLE 12

Preparation of Recombinant Human Interferon-β Modified with 5 kDa Three-chain Branched Polyethylene Glycol Abbreviation: 5PET(3UA)-rhIFN-β

In 2.0 ml of methylene chloride was dissolved 254 mg (0.02 mmol) of the compound of Example 4 (5PET(3UA)), and 5.9 mg (0.05 mmol) of NHS and 10.5 mg (0.05 mmol) of DCC were added thereto, followed by stirring in a stream of argon at 0° C. for one hour and at room temperature for 2 hours. The reaction mixture was added dropwise to diethyl ether, and the formed white precipitate was dried under reduced pressure to obtain 132.8 mg of NHS ester of the compound of Example 4 (yield: 52.3%).

To 1.0 ml of a 1.16 mg/ml solution of rhIFN-β obtained in Reference Example 4 in 20 mmol/l phosphate buffer (pH 7.8) containing ethylene glycol and sodium chloride was added 13 mg (15 mol per mol of protein) of the above NHS ester of 5PET(3UA), and the mixture was subjected to reaction a whole day and night at 4° C. The reaction mixture was applied to Sephadex G-25 column (Amersham-Pharmacia Biotech) and subjected to buffer exchange with 20 mmol/l phosphate buffer (pH 6) containing ethylene glycol. The mixture was passed through CM-Sepharose F.F. column (1.4 ml, Amersham-Pharmacia Biotech), followed by washing with 7.0 ml of 20 mmol/l phosphate buffer (pH 6) containing ethylene glycol. Elution was carried out with the same buffer containing 0.1 to 0.5 mol/l sodium chloride, and the desired fractions were combined and then concentrated to obtain 1.0 ml of a solution containing the desired substance (0.14 mg/ml) (yield: 12%).

<Electrophoresis>
SDS-PAGE was carried out in the presence of 2-mercaptoethanol in a manner similar to Example 9 to confirm the bands of 1 to 3 molecules-bound substances.

<Gel Filtration HPLC Analysis>
Analysis was carried out using two TSKgelG4000SW$_{XL}$ columns in a manner similar to Example 9.
Retention time: 43.8 minutes (1 molecule-bound substance)
41.2 minutes (2 molecules-bound substance)

EXAMPLE 13

Preparation of Recombinant Human Interferon-β Modified with 5 kDa Three-chain Branched Polyethylene Glycol Abbreviation: 5PET(3UA)-$^{17}$Ser rhIFN-β

To 0.05 ml of a 2.1 mg/ml solution of $^{17}$Ser rhIFN-β (Chiron) in 20 mmol/l phosphate buffer (pH 7.5) containing ethylene glycol and sodium chloride was added 1.6 mg (20 mol per mol of protein) of NHS ester of 5PET(3UA) obtained in a manner similar to Example 12, and the mixture was subjected to reaction a whole day and night at 4° C. The reaction mixture was applied to Sephadex G-25 column (Amersham-Pharmacia Biotech) and subjected to buffer exchange with 20 mmol/l phosphate buffer (pH 6) containing ethylene glycol. The fraction obtained by gel filtration was passed through CM-Sepharose F.F. column (0.5 ml, Amersham-Pharmacia Biotech), followed by washing with 8 ml of 20 mmol/l phosphate buffer (pH 6) containing ethylene glycol. Elution was carried out with the same buffer containing 0.2 to 1.0 mol/l sodium chloride, and the desired fractions were combined and then concentrated to obtain 0.30 ml of a solution containing the desired substance (27.8 µg/ml) (yield: 7.9%).

<Electrophoresis>

SDS-PAGE was carried out in the presence of 2-mercaptoethanol in a manner similar to Example 9 to confirm the bands of 1 to 3 molecules-bound substances.

EXAMPLE 14

Preparation of Recombinant Human Interferon-α Modified with 5 kDa Three-chain Branched Polyethylene Glycol Abbreviation: 5PET(3UA)-rhIFN-α

To 0.1 ml of a 1.0 mg/ml solution of rhIFN-α (IBL Co., Ltd.) in isotonic phosphate buffer (pH 7.5) was added 1.6 mg (20 mol per mol of protein) of NHS ester of 5PET(3UA) obtained in a manner similar to Example 12, and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (0.7 ml, Amersham-Pharmacia Biotech), followed by washing with 20 mmol/l sodium acetate buffer (pH 4.5). Elution was carried out with the same buffer containing 0.1 to 0.5 mol/l sodium chloride, and the desired fractions were combined and then concentrated to obtain 65 µl of a solution containing the desired substance (0.53 mg/ml) (yield: 34%).

<Electrophoresis>

SDS-PAGE was carried out in the presence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.

Retention time: 42.6 minutes (1 molecule-bound substance)
40.3 minutes (2 molecules-bound substance)

EXAMPLE 15

Preparation of Recombinant Human Granulocyte-colony Stimulating Factor Derivative Modified with 5 KDa Three-chain Branched Polyethylene Glycol Abbreviation: 5SKA(3UA)-rhG-CSF derivative In 100 µl of methylene chloride was dissolved 16 mg (1.1 µmol) of the compound of Example 2 (5SKA(3UA)), and 272 µg of DCC and 152 µg of NHS were added thereto, followed by stirring under ice-cooling for one hour and at room temperature for one hour. The reaction mixture was added dropwise to diethyl ether, and the formed white precipitate was dried under reduced pressure to obtain 14.5 mg of NHS ester of the compound of Example 2 (yield: 91%).

To 50 µl of a 3.7 mg/ml solution of the rhG-CSF derivative obtained in Reference Example 5 in 50 mmol/l phosphate buffer (pH 7.5) was added 3.6 mg (25 mol per mol of protein) of the compound activated above (NHS ester), and the mixture was subjected to reaction a whole day and night at 4° C. The reaction mixture was applied to Sephadex G-25 column (Amersham-Pharmacia Biotech) and subjected to buffer exchange with 20 mmol/l acetate buffer (pH 4.5), followed by purification using SP Sepharose F.F. column (0.7 ml, Amersham-Pharmacia Biotech). The desired fraction was concentrated to obtain 165 µl of a solution containing the desired substance (0.4 mg/ml) (yield: 36%).

<Electrophoresis>

SDS-PAGE was carried out in the absence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.

Retention time: 42.3 minutes (1 molecule-bound substance)
40.2 minutes (2 molecules-bound substance)

EXAMPLE 16

Preparation of a Solution Containing Recombinant Human Granulocyte-colony Stimulating Factor Modified with 5 KDa Four-chain Branched Polyethylene Glycol Abbreviation: 5QNA(4UA)-rhG-CSF derivative In 500 µl of methylene chloride was dissolved 69 mg (3.5 mmol) of the compound of Example 3 (5QNA(4UA)), and 1.8 mg of DSC and 0.56 mg of DMAP were added thereto, followed by stirring at room temperature for 6 hours. The reaction mixture was added dropwise to diethyl ether, and the formed white precipitate was dried under reduced pressure to obtain 44 mg of NHS ester of the compound of Example 3 (yield: 63%).

To 50 µl of a 3.8 mg/ml solution of the rhG-CSF derivative obtained in Reference Example 5 in 50 mmol/l phosphate buffer (pH 8) was added 5.1 mg (25 mol per mol of protein) of the compound activated above (NHS ester), and the mixture was subjected to reaction a whole day and night at 4° C. Without further purification steps, the resulting product was confirmed by electrophoresis and gel filtration HPLC analysis.

<Electrophoresis>
SDS-PAGE was carried out in the absence of 2-mercaptoethanol in a manner similar to Example 9 to confirm the band of 1 molecule-bound substance.

<Gel Filtration HPLC Analysis>
Analysis was carried out using two TSKgelG4000SW$_{XL}$ columns in a manner similar to Example 9.
Retention time: 40.8 minutes (1 molecule-bound substance)

EXAMPLE 17

Preparation of Recombinant Human Granulocyte-colony Stimulating Factor Modified with 5 KDa Three-chain Branched Polyethylene Glycol Abbreviation: 5SKA(3UA)-rhG-CSF In 100 μl of methylene chloride was dissolved 16 mg (1.1 μmol) of the compound of Example 2 (5SKA(3UA)), and 272 μg of DCC and 152 μg of NHS were added thereto, followed by stirring under ice-cooling for one hour and at room temperature for one hour. The reaction mixture was added dropwise to diethyl ether, and the formed white precipitate was dried under reduced pressure to obtain 14.5 mg of NHS ester of the compound of Example 2 (yield: 91%).

To 140 μl of a 4.4 mg/ml solution of the rhG-CSF obtained in Reference Example 6 in 50 mmol/l phosphate buffer (pH 7.5) was added 12.2 mg (25 mol per mol of protein) of the compound activated above (NHS ester), and the mixture was subjected to reaction a whole day and night at 4° C. The reaction mixture was applied to Sephadex G-25 column (Amersham-Pharmacia Biotech) and subjected to buffer exchange with 20 mmol/l acetate buffer (pH 4.5), followed by purification using SP Sepharose F.F. column (1.8 ml, Amersham-Pharmacia Biotech). The desired fraction was concentrated to obtain 110 μl of a solution containing the desired substance (1.1 mg/ml) (yield: 19%).

<Electrophoresis>
SDS-PAGE was carried out in the absence of 2-mercaptoethanol in a manner similar to Example 9 to confirm the bands of 1 to 3 molecules-bound substances.

<Gel Filtration HPLC Analysis>
Analysis was carried out using two TSKgelG4000SW$_{XL}$ columns in a manner similar to Example 9.
Retention time: 40 to 45 minutes (1 to 3 molecules-bound substances)

EXAMPLE 18

Preparation of Recombinant Human Granulocyte-colony Stimulating Factor Derivative Modified with 5 KDa Three-chain Branched Polyethylene Glycol Abbreviation: 5PET(3UU)-rhG-CSF derivative To 0.5 ml of a 3.1 mg/ml solution of the rhG-CSF derivative obtained in Reference Example 5 in 20 mmol/l phosphate buffer (pH 7.5) was added 12.2 mg (10 mol per mol of protein) of 5PET(3UU) obtained in Example 6, and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (1.5 ml, Amersham-Pharmacia Biotech), followed by washing with 7.5 ml of 20 mmol/l sodium acetate buffer (pH 4.5). Elution was carried out with the same buffer containing 0.2 to 0.5 mol/l sodium chloride, and the desired fractions were combined and then concentrated to obtain 0.75 ml of a solution containing the desired substance (1.2 mg/ml) (yield: 58.6%).

<Electrophoresis>
SDS-PAGE was carried out in the absence of 2-mercaptoethanol in a manner similar to Example 9 to confirm the bands of 1 to 3 molecules-bound substances.

<Gel Filtration HPLC Analysis>
Analysis was carried out using two TSKgelG4000SW$_{XL}$ columns in a manner similar to Example 9.
Retention time: 40.5 minutes (1 molecule-bound substance)
37.8 minutes (2 molecules-bound substance)

EXAMPLE 19

Preparation of Recombinant Human Granulocyte-colony Stimulating Factor Derivative Modified with 5 KDa Three-chain Branched Polyethylene Glycol Abbreviation: 5PET(3UA)-rhG-CSF Derivative To 0.05 ml of a 4.0 mg/ml solution of the rhG-CSF derivative obtained in Reference Example 5 in 20 mmol/l phosphate buffer (pH 7.5) was added 1.6 mg (10 mol per mol of protein) of NHS ester of 5PET(3UA) obtained in a manner similar to Example 12, and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (0.7 ml, Amersham-Pharmacia Biotech), followed by washing with 20 mmol/l sodium acetate buffer (pH 4.5). Elution was carried out with the same buffer containing 0.2 to 0.5 mol/l sodium chloride, and the desired fractions were combined and then concentrated to obtain 0.30 ml of a solution containing the desired substance (0.34 mg/ml) (yield: 56.7%).

<Electrophoresis>
SDS-PAGE was carried out in the absence of 2-mercaptoethanol in a manner similar to Example 9 to confirm the bands of 1 to 3 molecules-bound substances.

<Gel Filtration HPLC Analysis>
Analysis was carried out using two TSKgelG4000SW$_{XL}$ columns in a manner similar to Example 9.
Retention time: 42.3 minutes (1 molecule-bound substance)
39.5 minutes (2 molecules-bound substance)

EXAMPLE 20

Preparation of Recombinant Human Granulocyte-colony Stimulating Factor Derivative Modified with 5 kDa Three-chain Branched Polyethylene Glycol Abbreviation: 5SUG(3UA)-rhG-CSF Derivative To 100 mg (6.7 μmol) of the compound obtained in Example 8 (5SUG(3UA)) were added 2.3 mg of NHS and 4.1 mg of DCC, and the mixture was dissolved in 1 ml of methylene chloride under ice-cooling, followed by stirring under ice-cooling for one hour and at room temperature for 1.5 hours. The reaction mixture was added dropwise to diethyl ether and the formed white precipitate was dried under reduced pressure to obtain 76.6 mg of NHS ester of the compound of Example 8 (yield: 76.6%).

To 0.1 ml of a 3.9 mg/ml solution of the rhG-CSF derivative obtained in Reference Example 5 in 50 mmol/l phosphate buffer (pH 7.5) was added 10.7 mg (35 mol per mol of protein) of the compound activated above (NHS ester), and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (0.7 ml, Amersham-Pharmacia Biotech), followed by washing with 20 mmol/l sodium acetate buffer (pH 4.5). Elution was carried out with the same buffer containing 0.2 to 0.5 mol/l sodium chloride, and the desired fractions were combined and then concentrated to obtain 0.39 ml of a solution containing the desired substance (0.28 mg/ml) (yield: 27.8%).

<Electrophoresis>

SDS-PAGE was carried out in the absence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.

Retention time: 43.0 minutes (1 molecule-bound substance)
40.4 minutes (2 molecules-bound substance)

EXAMPLE 21

Preparation of Human Cu, Zn-superoxide Dismutase Modified with 5 kDa Three-chain Branched Polyethylene Glycol Abbreviation: 5PET(3UM)-hSOD To 0.5 ml of a 1.34 mg/ml solution of Cu, Zn-hSOD (CELLULAR PRODUCTS, INC.) in 50 mmol/l phosphate buffer (pH 7.5) was added 3.1 mg (10 mol per mol of protein) of 5PET(3UM) obtained in Example 5, and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 3.5). The mixture was passed through SP-Sepharose F.F. column (0.7 ml, Amersham-Pharmacia Biotech), followed by washing with 20 mmol/l sodium acetate buffer (pH 3.5). Elution was carried out with the same buffer containing 0.5 to 1.0 mol/l sodium chloride, and the desired fractions were combined and then concentrated to obtain 0.62 ml of a solution containing the desired substance (0.33 mg/ml) (yield: 30.6%).

<Electrophoresis>

SDS-PAGE was carried out in the absence of 2-mercaptoethanol in a manner similar to Example 9 to confirm the band of 1 molecule-bound substance.

<Gel Filtration HPLC Analysis>

Analysis was carried out using two TSKgelG4000SW$_{XL}$ columns in a manner similar to Example 9.

Retention time: 41.1 minutes (1 molecule-bound substance)

EXAMPLE 22

Preparation of Anti-GD3 Chimera Antibody Modified with 5 kDa Three-chain Branched Polyethylene Glycol Abbreviation: 5PET(3UA)-KM871

To 1.0 ml of a 1.1 mg/ml solution of anti-GD3 chimera antibody (KM-871) in 20 mmol/l phosphate buffer (pH 7.5) (prepared according to Japanese Published Unexamined Patent Application No. 304989/93) was added 0.6 mg (5 mol per mol of protein) of NHS ester of 5PET(3UA) obtained in a manner similar to Example 12, and the mixture was subjected to reaction a whole day and night at 4° C. The reaction mixture (1.0 ml) was applied to Sephadex G-25 column (Amersham-Pharmacia Biotech) and subjected to buffer exchange with 20 mmol/l acetate buffer (pH 4.5). The mixture was passed through CM-Sepharose F.F. column (1.0 ml, Amersham-Pharmacia Biotech), followed by washing with 20 mmol/l sodium acetate buffer (pH 4.5). Elution was carried out with the same buffer containing 0.25 to 1.0 mol/l sodium chloride, and the desired fractions were combined and then concentrated to obtain 430 µl of a solution containing the desired substance (0.52 mg/ml) (yield: 20.4%).

<Electrophoresis>

SDS-PAGE was carried out in the absence of 2-mercaptoethanol in a manner similar to Example 9 to confirm the bands of 1 to 2 molecules-bound substances.

EXAMPLE 23

Preparation of Recombinant Human Granulocyte-colony Stimulating Factor Derivative Modified with 5 KDa Three-chain Branched Polyethylene Glycol Abbreviation: 5PET(3URa)-rhG-CSF Derivative To 0.6 ml of a 2.35 mg/ml solution of the rhG-CSF derivative obtained in Reference Example 5 in 50 mmol/l phosphate buffer (pH 7.5) were added 56.3 mg (50 mol per mol of protein) of the compound of Example 7 (5PET(3URa)) and 10 µl of a 120 mmol/l aqueous NaBH$_3$CN solution. The mixture was subjected to reaction a whole day and night at 4° C. and then made acidic with hydrochloric acid to stop the reaction. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (1.4 ml, Amersham-Pharmacia Biotech), followed by washing with 20 mmol/l sodium acetate buffer (pH 4.5). Elution was carried out with the same buffer containing 0.1 to 0.2 mol/l sodium chloride, and the desired fractions were combined and then concentrated to obtain 0.55 ml of a solution containing the desired substance (0.24 mg/ml) (yield: 8.5%).

<Electrophoresis>

SDS-PAGE was carried out in the absence of 2-mercaptoethanol in a manner similar to Example 9 to confirm the band of 1 molecule-bound substance.

<Gel Filtration HPLC Analysis>

Analysis was carried out using two TSKgelG4000SW$_{XL}$ columns in a manner similar to Example 9.

Retention time: 41.2 minutes (1 molecule-bound substance)

REFERENCE EXAMPLE 1

Preparation of Recombinant Human Interferon-β Modified with 5 kDa Double-chain Branched Polyethylene Glycol (A Conventional Reagent)

Abbreviation: PEG$_2$Lys-rhIFN-β

To 1.3 ml of a 0.97 mg/ml solution of rhIFN-β obtained in Reference Example 4 in 20 mmol/l phosphate buffer (pH 7.8) containing ethylene glycol and sodium chloride was added 8.3 mg (12.5 mol per mol of protein) of PEG$_2$Lys (average molecular weight: 10,000, Shearwater Polymers, Inc.), and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 6) containing ethylene glycol. The mixture was passed through CM-Sepharose F.F. column (1.4 ml, Amersham-Pharmacia Biotech), followed by washing with 20 mmol/l sodium acetate buffer (pH 6) containing ethylene glycol. Elution was carried out with the same buffer containing 0.1 to 0.5 mol/l sodium chloride, and the desired fractions were combined and then concentrated to obtain 2.7 ml of a solution containing the desired substance (0.36 mg/ml) (yield: 76.7%).

<Electrophoresis>

SDS-PAGE was carried out in the presence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.
Retention time: 45.3 minutes (1 molecule-bound substance)
41.5 minutes (2 molecules-bound substance)

REFERENCE EXAMPLE 2

Preparation of Recombinant Human Granulocyte-colony Stimulating Factor Derivative Modified with 5 KDa Double-chain Branched Polyethylene Glycol (a Conventional Reagent)

Abbreviation: PEG$_2$Lys-rhG-CSF derivative

To 0.5 ml of a 4.0 mg/ml solution of the rhG-CSF derivative obtained in Reference Example 5 in 50 mmol/l phosphate buffer (pH 7.5) was added 10.6 mg (10 mol per mol of protein) of PEG$_2$Lys (average molecular weight: 10,000, Shearwater Polymers, Inc.), and the mixture was subjected to reaction a whole day and night at 4° C. The reaction mixture was applied to Sephadex G-25 column (Amersham-Pharmacia Biotech) and subjected to buffer exchange with 20 mmol/l sodium acetate buffer (pH 4.5). The mixture was passed through SP-Sepharose F.F. column (2.0 ml, Amersham-Pharmacia Biotech), followed by washing with 10 ml of 20 mmol/l sodium acetate buffer (pH 4.5). Elution was carried out with the same buffer containing 0.2 to 0.5 mol/l sodium chloride, and the desired fractions were combined and then concentrated to obtain 0.5 ml of a solution containing the desired substance (1.05 mg/ml) (yield: 26.3%).

<Electrophoresis>

SDS-PAGE was carried out in the absence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.
Retention time: 44.3 minutes (1 molecule-bound substance)
41.7 minutes (2 molecules-bound substance)

REFERENCE EXAMPLE 3

Preparation of Recombinant Human Granulocyte-colony Stimulating Factor Modified with 5 KDa Single-chain Polyethylene Glycol (a Conventional Reagent)

Abbreviation: PEG$_2$Lys-rhG-CSF

To 0.5 ml of a 4.4 mg/ml solution of rhG-CSF obtained in Reference Example 6 in isotonic phosphate buffer (pH 7.4) was added 11.7 mg (10 mol per mol of protein) of PEG$_2$Lys (average molecular weight: 10,000, Shearwater Polymers, Inc.), and the mixture was subjected to reaction a whole day and night at 4° C. The reaction mixture was applied to Sephadex G-25 column (Amersham-Pharmacia Biotech) and subjected to buffer exchange with 20 mmol/l acetate buffer (pH 4.5). The mixture was passed through SP-Sepharose F.F. column (2.0 ml, Amersham-Pharmacia Biotech), followed by washing with 10 ml of 20 mmol/l sodium acetate buffer (pH 4.5). Elution was carried out with the same buffer containing 0.2 to 0.5 mol/l sodium chloride, and the desired fractions were combined and then concentrated to obtain 0.5 ml of a solution containing the desired substance (1.78 mg/ml) (yield: 40.5%).

<Electrophoresis>

SDS-PAGE was carried out in the absence of 2-mercaptoethanol in a manner similar to Example 9 to confirm the bands of 1 to 3 molecules-bound substances.

<Gel Filtration HPLC Analysis>

Analysis was carried out using two TSKgelG4000SW$_{XL}$ columns in a manner similar to Example 9.
Retention time: 44.2 minutes (1 molecule-bound substance)
41.8 minutes (2 molecules-bound substance)

REFERENCE EXAMPLE 4

Preparation of Recombinant Human Interferon-β (Unmodified rhIFN-β)

rhIFN-β having the amino acid sequence shown in SEQ ID NO: 1 was produced according to the method of Mizukami, et al. [Biotechnology Letter, Vol. 8, p. 605 (1986)] and the method of Kuga, et al. [Chemistry Today, extra number 12: Gene Engineering in Medical Science, p. 135 (1986), Tokyo Kagaku Dojin].

*Escherichia coli* K-12 carrying plasmid pMG-1 comprising DNA encoding rhIFN-β was seed-cultured in LGTrpAp medium (10 g/l bactotrypton, 5 g/l yeast extract, 5 g/l sodium chloride, 1 g/l glucose, 50 mg/l L-tryptophan and 50 μg/l ampicillin). For the production of rhIFN-β, culturing was carried out in a 2-l jar fermenter using MCGAp medium (a medium prepared by adding 0.5% Casamino acid and 50 μg/ml ampicillin to M9 medium) at 20° C. for several days, during which the glucose concentration was maintained at 1% and pH at 6.5. The culture was shaken at 750 rpm and aerated at 1 l/minute. From the culture, an extract was prepared by the freezing and thawing method [DNA, Vol. 2, p. 265 (1983)]. Further, rhIFN-β was obtained from the cell residue according to the method disclosed in Japanese Published Unexamined Patent Application No. 69799/86.

REFERENCE EXAMPLE 5

Preparation of Recombinant Human Granulocyte-colony Stimulating Factor Derivative (Unmodified rhG-CSF Derivative)

An rhG-CSF derivative wherein threonine at position 1 was replaced with alanine, leucine at position 3 was replaced with threonine, glycine at position 4 was replaced with tyrosine, proline at position 5 was replaced with arginine and cysteine at position 17 was replaced with serine in hG-CSF having the amino acid sequence shown in SEQ ID NO: 2 was obtained by the method described in Japanese Published Examined Patent Application No. 96558/95.

*Escherichia coli* W3110strA carrying plasmid pCfBD28 comprising DNA encoding the above rhG-CSF derivative (*Escherihica coli* ECfBD28 FERM BP-1479) was cultured in LG medium (a medium prepared by dissolving 10 g of bactotrypton, 5 g of yeast extract, 5 g of sodium chloride and 1 g of glucose in 1 L of water and adjusted to pH 7.0 with NaOH) at 37° C. for 18 hours. The resulting culture (5 ml) was inoculated into 100 ml of MCG medium (0.6% $Na_2HPO_4$, 0.3% $KH_2PO_4$, 0.5% sodium chloride, 0.5% Casamino acid, 1 mmol/l $MgSO_4$, 14 µg/ml vitamin B, pH 7.2) containing 25 µg/ml tryptophan and 50 µg/ml ampicillin. After culturing at 30° C. for 4 to 8 hours, 10 µg/ml 3β-indoleacrylic acid (hereinafter abbreviated as IAA), a tryptophan inducer, was added, followed by further culturing for 2 to 12 hours. The obtained culture was centrifuged at 8,000 rpm for 10 minutes to collect cells, and the cells were washed with a 30 mmol/l aqueous solution of sodium chloride and 30 mmol/l tris-hydrochloride buffer (pH 7.5). The washed cells were suspended in 30 ml of the above buffer and disrupted by ultrasonication (BRANSON SONIC POWER COMPANY, SONIFIER CELL DISRUPTOR 200, OUTPUT CONTROL 2) at 0° C. for 10 minutes. The ultrasonicated cells were centrifuged at 9,000 rpm for 30 minutes to obtain cell residue.

From the cell residue, the rhG-CSF derivative was extracted, purified, solubilized and regenerated in accordance with the method of Marston, et al. [BIO/TECHNOLOGY, Vol. 2, p. 800 (1984)].

REFERENCE EXAMPLE 6

Preparation of Recombinant Human Granulocyte-colony Stimulating Factor (Unmodified rhG-CSF)

rhG-CSF having the amino acid sequence shown in SEQ ID NO: 2 was prepared according to the method described in Reference Example 5.

TEST EXAMPLE 1

Antiviral Activity of Chemically Modified Interferon-β

The antiviral activity of the chemically modified rhIFN-β obtained in Examples 9, 10, 12 and 13 and unmodified rhIFN-β was examined by the following neutral red (NR) uptake method.

<NR Uptake Method>

The antiviral activity was measured by referring to the method of Kohase, et al. [Protein, Nucleic Acid and Enzyme (extra number), p. 335 (1981)].

That is, 5% fetal bovine serum (FBS)-supplemented Eagle's MEM was added to a sterilized transfer plate. Then, 50 µl each of solutions of domestic standard IFN preparations [α (The Green Cross Corporation), β (Toray Industries, Inc.) and γ (The Green Cross Corporation)] were put into wells, followed by 2-fold serial dilution. On the other hand, 50 µl each of chemically modified IFNs and unmodified IFNs diluted with a medium to predetermined concentrations were put into wells. These IFN solutions were transferred to a 96-well plate containing a predetermined cell number of an established cell line (FL cell) derived from human amnion, followed by stirring for several seconds. The resulting mixtures were incubated a whole day and night in a $CO_2$ incubator at 37° C. to induce an antiviral state.

Then, the culture liquors were removed, and a virus solution was added, followed by incubation in a $CO_2$ incubator at 37° C. for 2 days to effect viral infection. The antiviral state of the cells was changed by IFN, and cell degeneration occurred. Subsequently, the culture liquors were removed, and a neutral red (NR) solution was added. The plate was allowed to stand in a $CO_2$ incubator at 37° C. for one hour, followed by removal of the NR solution. After the wells were washed with an isotonic phosphate buffer, an extracting liquid (0.01 mol/l hydrochloric acid—30% ethanol) was added, followed by stirring for 2 to 3 minutes.

The surviving cells were stained with NR. After extraction, the absorbance at 492 nm was measured, and a standard curve was plotted. The relative activity of each chemically modified IFN was calculated based on the activity of the unmodified IFN calculated from the standard curve which was defined as 100%.

The relative activity of each IFN-β is shown in Tables 5 and 6.

TABLE 5

Antiviral activity of chemically modified recombinant human IFN-β

| Compound abbreviation | Example | Relative activity (%) |
| --- | --- | --- |
| Unmodified rhIFN-β | — | 100 |
| 5TRC (3UA)-rhIFN-β | 9 | 58 |
| 5SKA (3UA)-rhIFN-β | 10 | 93 |
| 5PET (3UA)-rhIFN-β | 12 | 50 |

TABLE 6

Antiviral activity of chemically modified recombinant human $^{17}$Ser IFN-β

| Compound abbreviation | Example | Relative activity (%) |
| --- | --- | --- |
| Unmodified $^{17}$Ser rhIFN-β | — | 100 |
| 5PET (3UA)-$^{17}$Ser rhIFN-β | 13 | 115 |

It was confirmed by the results in Tables 5 and 6 that all the chemically modified IFN-β according to the present invention retained antiviral activity.

TEST EXAMPLE 2

Antiviral Activity of Chemically Modified Interferon-α

The antiviral activity of the chemically modified rhIFN-α obtained in Example 14 and unmodified rhIFN-α was examined by the NR uptake method illustrated in Test Example 1.

The activity of each IFN-α at a concentration of 1 μg/ml is shown in Table 7 (indicated as a relative activity based on the activity of unmodified IFN-α defined as 100%).

TABLE 7

Antiviral activity of chemically modified recombinant human IFN-α

| Compound abbreviation | Example | Concentration (μg/ml) | Relative activity (%) |
|---|---|---|---|
| Unmodified rhIFN-α | — | 1 | 100 |
| 5PET (3UA)-rhIFN-α | 14 | 1 | 100 |

TEST EXAMPLE 3

Growth-promoting Activity of Chemically Modified Recombinant Human Granulocyte-colony Stimulating Factor Derivative on Mouse Leukemia Cell NFS60

The growth-promoting activity of the compounds of Examples 15 to 20, unmodified rhG-CSF derivative and unmodified rhG-CSF on mouse leukemia cell NFS60 [Proc. Natl. Acad. Sci. USA, Vol. 82, p. 6687 (1985)] was measured according to the method of Asano, et al. [Japanese Pharmacology & Therapeutics, Vol. 19, p. 2767 (1991)].

The activity of each compound at a concentration of 100 ng/ml is shown in Tables 8 and 9 as a relative activity based on the activity of unmodified polypeptide defined as 100%.

TABLE 8

NFS60 cell growth-promoting activity of chemically modified rhG-CSF derivatives

| Compound abbreviation | Example | Concentration (ng/ml) | Relative activity (%) |
|---|---|---|---|
| Unmodified rhG-CSF deriv. | — | 100 | 100 |
| 5SKA (3UA)-rhG-CSF deriv. | 15 | 100 | 100 |
| 5QNA (4UA)-rhG-CSF deriv. | 16 | 100 | 100 |
| 5PET (3UU)-rhG-CSF deriv. | 18 | 100 | 100 |
| 5PET (3UA)-rhG-CSF deriv. | 19 | 100 | 100 |
| 5SUG (3UA)-rhG-CSF deriv. | 20 | 100 | 100 |

TABLE 9

NFS60 cell growth-promoting activity of chemically modified rhG-CSF

| Compound abbreviation | Example | Concentration (ng/ml) | Relative activity (%) |
|---|---|---|---|
| Unmodified rhG-CSF | — | 100 | 100 |
| 5SKA (3UA)-rhG-CSF | 17 | 100 | 100 |

It was confirmed by the results in Tables 8 and 9 that all the chemically modified rhG-CSF derivatives and chemically modified rhG-CSF according to the present invention retained growth-promoting activity on NFS60 cells.

TEST EXAMPLE 4

Enzyme Activity of Chemically Modified Superoxide Dismutase

The enzyme activity of the chemically modified SOD prepared in Example 21 was measured by the xanthine-xanthine oxidase-cytochrome C system of Mccord, J. M. and Fridovichi, I. [J. Biol. Chem., Vol. 244, p. 6049 (1969)]. One unit (U) of SOD activity is an enzyme amount of SOD which inhibits the reducing rate of cytochrome C by 50% at pH 7.8 at 30° C., and was calculated according to the following equation.

$$\text{Specific activity (U/mg)} = \left(\frac{\text{blank}}{\Delta A/\min} - 1\right) \times \frac{1}{0.000256}$$

The enzyme activity of chemically modified human SOD is shown in Table 10.

SOD 50 U/ml=0.000256 mg (at 3900 U/mg)
ΔA/min.: measurement result

TABLE 10

Enzyme activity of chemically modified human Cu, Zn-superoxide dismutase

| Compound | Example | Relative activity (%) |
|---|---|---|
| Unmodified hSOD | — | 100 |
| 5PET (3UM)-hSOD | 21 | 50 |

*The activity was indicated as a relative activity based on the enzyme activity of unmodified hSOD defined as 100%.

It was confirmed by Table 10 that chemically modified hSOD according to the present invention retained enzyme activity.

TEST EXAMPLE 5

Binding Activity of Chemically Modified Anti-GD3 Chimera Antibody

The binding activity of the chemically modified anti-GD3 chimera antibody (5PET(3UA)-KM871) prepared in Example 22 was measured according to the method of Kenya. S, et al. [Cancer Immunol. Immunother., Vol. 36, p. 373 (1993)].

The GD3-binding activity of unmodified antibody and chemically modified anti-GD3 chimera antibody (5PET (3UA)-KM871) at a concentration of 3.3 g/ml is shown in Table 11.

The activity was indicated as a relative activity based on the binding activity of unmodified anti-GD3 chimera antibody defined as 100%.

TABLE 11

GD3-Binding activity of chemically modified antibody

| Compound | Example | Relative binding activity (%) |
|---|---|---|
| Unmodified antibody | — | 100 |
| 5PET (3UA)-KM871 | 22 | 86.3 |

It was confirmed by Table 11 that the chemically modified anti-GD3 chimera antibody (5PET(3UA)-KM871) according to the present invention retained GD3-binding activity.

TEST EXAMPLE 6

Blood half-life Prolonging Effect of Chemically Modified Interferon-β

Each of 5TRC(3UA)-rhIFN-β obtained in Example 9, PEG₂Lys-rhIFN-β obtained in Reference Example 1 and unmodified rhIFN-β obtained in Reference Example 4 was dissolved in an isotonic phosphate buffer at a concentration of 12.5 μg/ml, and 200 μl of each of the solutions was intravenously injected into 8 to 10-week-old BALB/C male mice (Charles River Japan, Inc.). At intervals, the mice were killed and the serum was collected. The IFN-β concentration in blood was calculated by ELISA.

The result is shown in FIG. 1.

The concentration of unmodified IFN-β fell below the detection limit in one hour after the administration, whereas the concentration of chemically modified IFN-β was maintained for several hours, showing a remarkable improvement in durability.

Moreover, the compound disclosed in the present invention, i.e. rhIFN-β modified with three-chain branched polyethylene glycol was superior in durability in blood to rhIFN-β modified with double-chain branched polyethylene glycol, and its concentration in blood changed at a higher level.

TEST EXAMPLE 7

Blood Half-life Prolonging Effect of Chemically Modified rhG-CSF

Figure 2:
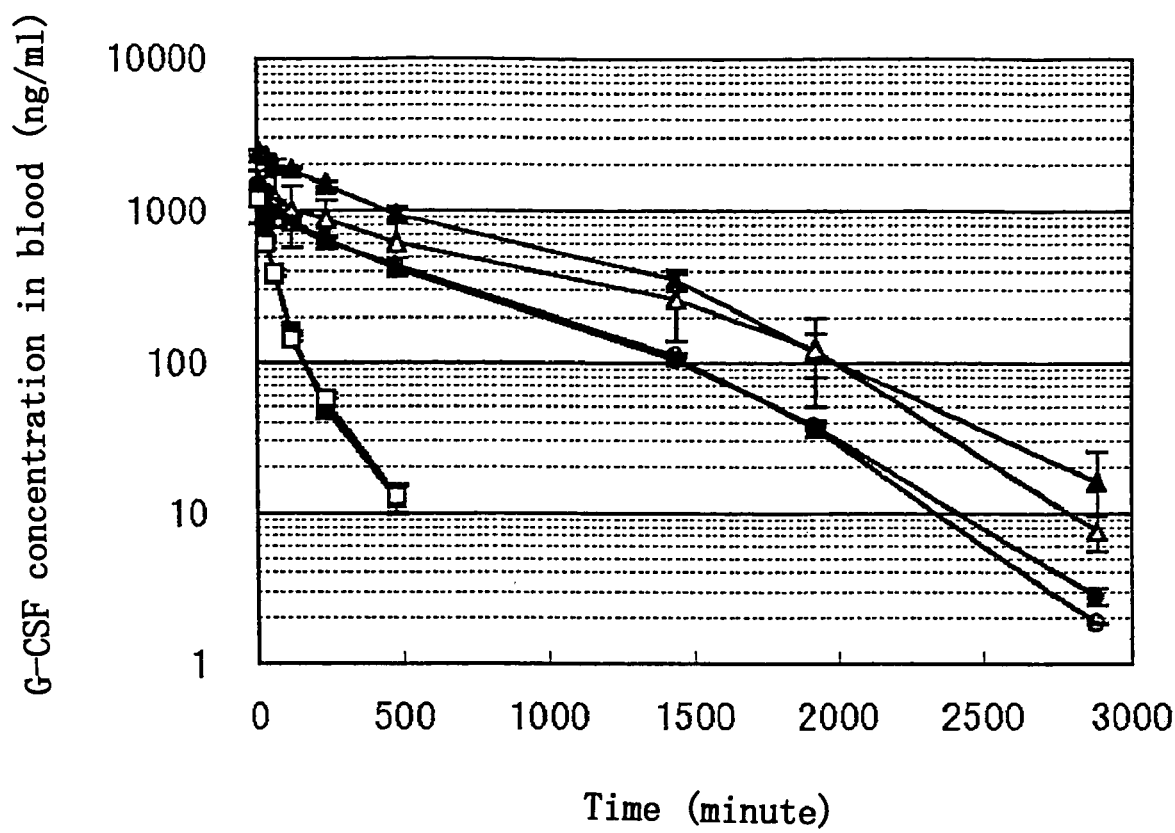
FIG. 2 shows the blood half-life prolonging effect of chemically modified recombinant human granulocyte-colony stimulating factors when intravenously injected into rats.
- ■ -: change in the concentration of unmodified rhG-CSF derivative in blood
- □ -: change in the concentration of unmodified rhG-CSF in blood
- ▲ -: change in the concentration of 5SKA(3UA)-rhG-CSF derivative in blood
- △ -: change in the concentration of 5SKA(3UA)-rhG-CSF in blood
- ● -: change in the concentration of PEG$_2$Lys-rhG-CSF derivative in blood
- ○ -: change in the concentration of PEG$_2$Lys-rhG-CSF in blood

Each of 5SKA(3UA)-rhG-CSF derivative obtained in Example 15, 5SKA(3UA)-rhG-CSF obtained in Example 17, PEG₂Lys-rhG-CSF derivative obtained in Reference Example 2, PEG₂Lys-rhG-CSF obtained in Reference Example 3, unmodified rhG-CSF derivative of Reference Example 5 and unmodified rhG-CSF of Reference Example 6 was intravenously injected into male rats at a dose of 0.1 mg/kg. At intervals, blood was collected from the tail vein. The blood was appropriately diluted and the concentration of each compound in the blood was measured by ELISA. The result obtained by duplicate experiments is shown in FIG. 2.

The chemically modified G-CSFs maintained much higher concentration in blood as compared with the unmodified G-CSFs. Moreover, it was confirmed that the compounds disclosed in the present invention, i.e. rhG-CSFs modified with three-chain branched polyethylene glycol were superior in durability in blood to the compounds modified with conventional double-chain branched polyethylene glycol.

INDUSTRIAL APPLICABILITY

The novel polyalkylene glycols having a branched structure disclosed in the present invention are useful as chemical modifying reagents for physiologically active polypeptides. The physiologically active peptides modified with the polyalkylene glycols not only retain biological activities similar to those of unmodified peptides, but show their physiological activities effectively for a long time when administered into the body. Therefore, the modified polypeptides are useful for improving or treating clinical conditions associated with their physiological activities.

The invention claimed is:

1. A branched polyalkylene glycol represented by formula (I):

(R¹-Mₙ-X¹)ₘL(X²—X³—R²)_q   (I)

wherein L represents

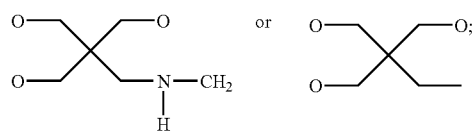

M represents OCH₂CH₂, OCH₂CH₂CH₂, OCH(CH₃)CH₂, (OCH₂CH₂)_r—(OCH₂CH₂CH₂)_s (in which r and s, independently represent a positive integer) or (OCH₂CH₂)_{ra}—[OCH(CH₃)CH₂]_{sa} (in which ra and sa independently represent a positive integer);

n represents a positive integer;

m represents 3;

q represents 1;

R¹ represents a hydrogen atom, lower alkyl or lower alkanoyl;

R² represents a group having reactivity with an amino acid side chain, the N-terminal amino group or the C-terminal carboxyl group in a polypeptide, or a group convertible into the group having reactivity;

X¹ represents —CH₂—NH(C=O)—;

X² represents a bond, O or (CH₂)_{te}O (in which te represents an integer of 1 to 8);

X³ represents a bond or alkylene; and three or more R¹-Mₙ-X¹'s may be the same or different, and when q is 2 or 3, X²—X³—R²'s may be the same or different.

2. The branched polyalkylene glycol according to claim 1, wherein L is

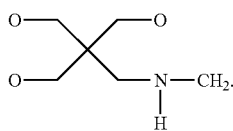

3. The branched polyalkylene glycol according to claim 1, wherein L is

4. The branched polyalkylene glycol according to claim 2 or 3, wherein n is 10 to 100,000, and r, s, ra and sa are independently 1 to 100,000.

5. The branched polyalkylene glycol according to claim 4, wherein $R^2$ is a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryldisulfido, or azido.

6. The branched polyalkylene glycol according to claim 5, which has a molecular weight of 500 to 1,000,000.

7. A chemically modified polypeptide comprising a physiologically active polypeptide or its derivative containing at least one branched polyalkylene glycol according to claim 2 or 3.

8. The chemically modified polypeptide according to claim 7, wherein the physiologically active polypeptide is an enzyme, a cytokine or a hormone.

9. A pharmaceutical composition comprising the chemically modified polypeptide according to claim 8 and a pharmaceutically acceptable carrier.

* * * * *

UNITED STATES PATENT AND TRADEMARK OFFICE
CERTIFICATE OF CORRECTION

PATENT NO. : 7,291,713 B2
APPLICATION NO. : 10/470680
DATED : November 6, 2007
INVENTOR(S) : Motoo Yamasaki et al.

It is certified that error appears in the above-identified patent and that said Letters Patent is hereby corrected as shown below:

ON THE TITLE PAGE ITEM [56] REFERENCES CITED:

Item 56 Foreign Patent Documents, "JP 153088 6/1989" should read --JP 1-153088 6/1989--; and Item 56 Other Publications, after "Conforti et al.": "Pelurisy" should read --Pleurisy-- and insert --Zalipsky, "Functionalized Poly(ethylene glycol) for Preparation of Biologically Relevant Conjugates", Bioconjugate Chem. Vol. 6, No. 2 (1995) pp. 150-165--.

COLUMN 11:

Line 42, "1" should read --one--.

COLUMN 14:

Line 43, "$(R^1-M_n-X_{1a})_m L(X^2-X^3-R^{2b})$ (Ian)" should read --$(R^1-M_n-X^{1a})_m L(X^2-X^3-R^{2b})_q$" (Ian)--.

COLUMN 27:

Line 15, "$CDCl_3) > \delta$" should read --$CDCl_3) > \P \delta$--; and
Line 46, "$CDCl_3) > \delta$ (ppm):" should read --$CDCl_3) > \P \delta$ (ppm):--.

COLUMN 28:

Line 14, "$CDCl_3) >$ Compound" should read --$CDCl_3) > \P$ Compound--; and
Line 51, "$CDCl_3) > \delta$" should read --$CDCl_3) > \P \delta$--.

COLUMN 29:

Line 28, "$CDCl_3) > \delta$" should read --$CDCl_3) > \P \delta$--.

COLUMN 30:

Line 1, "$CDCl_3) > \delta$" should read --$CDCl_3) > \P \delta$--.

UNITED STATES PATENT AND TRADEMARK OFFICE
CERTIFICATE OF CORRECTION

PATENT NO. : 7,291,713 B2
APPLICATION NO. : 10/470680
DATED : November 6, 2007
INVENTOR(S) : Motoo Yamasaki et al.

It is certified that error appears in the above-identified patent and that said Letters Patent is hereby corrected as shown below:

COLUMN 31:

Line 3, "$CDCl_3$) > δ" should read --$CDCl_3$) > ¶ δ--;
Line 16, "300 MHz) > δ" should read --300 MHz) > ¶ δ--;
Line 35, "300 MHz) > δ" should read --300 MHz) > ¶ δ--;
Line 47, "300 MHz) > δ" should read --300 MHz) > ¶ δ--;
Line 49, "1H) < Mass" should read --1H) ¶ < Mass--; and
Line 50, "FAB-MS) > Found:" should read --FAB-MS) > ¶ Found:-- and
"[M+H]=253 Calcd.:" should read --[M+H]=253 ¶ Calcd.:--.

COLUMN 32:

Line 13, "$CDCl_3$) > Compound" should read --$CDCl_3$) > ¶ Compound--; and
Line 15, "7H) Compound" should read --7H) ¶ Compound--.

COLUMN 49:

Line 67, "s," should read --s--.

Signed and Sealed this

Third Day of June, 2008

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 166
<212> TYPE: PRT
<213> ORGANISM: Hominidae

<400> SEQUENCE: 1

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Leu Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125
```

```
Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 175
<212> TYPE: PRT
<213> ORGANISM: Hominidae

<400> SEQUENCE: 2

Met Thr Pro Leu Gly Pro Ala Ser Ser Leu Pro Gln Ser Phe Leu Leu
 -1   1               5                  10                  15

Lys Cys Leu Glu Gln Val Arg Lys Ile Gln Gly Asp Gly Ala Ala Leu
                 20                  25                  30

Gln Glu Lys Leu Cys Ala Thr Tyr Lys Leu Cys His Pro Glu Glu Leu
             35                  40                  45

Val Leu Leu Gly His Ser Leu Gly Ile Pro Trp Ala Pro Leu Ser Ser
         50                  55                  60

Cys Pro Ser Gln Ala Leu Gln Leu Ala Gly Cys Leu Ser Gln Leu His
     65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
             115                 120                 125

Pro Ala Leu Gln Pro Thr Gln Gly Ala Met Pro Ala Phe Ala Ser Ala
             130                 135                 140

Phe Gln Arg Arg Ala Gly Gly Val Leu Val Ala Ser His Leu Gln Ser
     145                 150                 155

Phe Leu Glu Val Ser Tyr Arg Val Leu Arg His Leu Ala Gln Pro
160                 165                 170
```